(12) United States Patent
Yodfat et al.

(10) Patent No.: US 8,147,446 B2
(45) Date of Patent: Apr. 3, 2012

(54) DETACHABLE PORTABLE INFUSION DEVICE

(75) Inventors: Ofer Yodfat, Maccabim-Reut (IL); Danna Perlman, Haifa (IL)

(73) Assignee: Medingo Ltd., Yoqneam Illit (IL)

( * ) Notice: Subject to any disclaimer, the term of this patent is extended or adjusted under 35 U.S.C. 154(b) by 0 days.

(21) Appl. No.: 12/452,926

(22) PCT Filed: Jul. 31, 2008

(86) PCT No.: PCT/IL2008/001056
§ 371 (c)(1),
(2), (4) Date: Jan. 29, 2010

(87) PCT Pub. No.: WO2009/016635
PCT Pub. Date: Feb. 5, 2009

(65) Prior Publication Data
US 2010/0137790 A1    Jun. 3, 2010

Related U.S. Application Data

(60) Provisional application No. 60/963,045, filed on Aug. 1, 2007, provisional application No. 60/999,654, filed on Oct. 19, 2007.

(51) Int. Cl.
*A61M 5/168* (2006.01)
(52) U.S. Cl. ............... 604/67; 604/65; 604/66; 604/131
(58) Field of Classification Search ............ 604/65–67, 604/131, 19, 151; 600/365, 316, 347
See application file for complete search history.

(56) References Cited

U.S. PATENT DOCUMENTS

| 3,771,694 A | 11/1973 | Kaminski |
| 4,498,843 A | 2/1985 | Schneider et al. |
| 4,657,486 A | 4/1987 | Stempfle et al. |
| 5,957,895 A | 9/1999 | Sage et al. |

(Continued)

FOREIGN PATENT DOCUMENTS
WO    WO 2006/097453    9/2006
(Continued)

OTHER PUBLICATIONS

Written Opinion for PCT Application No. PCT/IL2008/001056.

*Primary Examiner* — Nicholas Lucchesi
*Assistant Examiner* — Quynh-Nhu H Vu
(74) *Attorney, Agent, or Firm* — Mintz Levin Cohn Ferris Glovsky and Popeo, P.C.

(57) ABSTRACT

A portable therapeutic apparatus and a method for controlling the apparatus are provided. In one aspect the apparatus and the method can be implemented using a patch unit (100, 200) removably attachable to a cradle unit (20), said cradle unit removably attachable to the body of the patient; a position detector (1000) comprising a patch portion (900) and a cradle portion (800), said patch portion coupled to the patch unit, said cradle portion coupled to the cradle unit; a processor adapted for receiving a position indication signal from the at least one position detector, said position indication signal corresponding to a physical proximity of the patch portion to the cradle portion, and, wherein the portable therapeutic apparatus is adapted for at least one therapeutic function selected from the group consisting of delivering a therapeutic fluid into the body of the patient and sensing a bodily analyte.

22 Claims, 26 Drawing Sheets

U.S. PATENT DOCUMENTS

| | | |
|---|---|---|
| 6,485,461 B1 | 11/2002 | Mason et al. |
| 6,589,229 B1 | 7/2003 | Connelly et al. |
| 6,723,072 B2 | 4/2004 | Flaherty et al. |
| 6,740,059 B2 | 5/2004 | Flaherty |
| 6,749,587 B2 * | 6/2004 | Flaherty ..................... 604/151 |
| 2002/0169439 A1 | 11/2002 | Flaherty |
| 2003/0088238 A1 | 5/2003 | Poulsen et al. |
| 2007/0106218 A1 | 5/2007 | Yodfat et al. |
| 2007/0191702 A1 | 8/2007 | Yodfat et al. |
| 2008/0021395 A1 | 1/2008 | Yodfat et al. |
| 2008/0077081 A1 * | 3/2008 | Mounce et al. ............. 604/67 |
| 2008/0215035 A1 | 9/2008 | Yodfat et al. |
| 2008/0319414 A1 | 12/2008 | Yodfat et al. |
| 2008/0319416 A1 | 12/2008 | Yodfat et al. |

FOREIGN PATENT DOCUMENTS

| | | |
|---|---|---|
| WO | WO 2007/056504 | 5/2007 |
| WO | WO 2007/071255 | 6/2007 |
| WO | WO 2008/029403 | 3/2008 |
| WO | WO 2008/038274 | 4/2008 |
| WO | WO 2008/139458 | 11/2008 |
| WO | WO 2009/013736 | 1/2009 |
| WO | WO 2009/016636 | 2/2009 |

* cited by examiner

DETACHABLE PORTABLE INFUSION DEVICE

CROSS-REFERENCE TO RELATED APPLICATIONS

The present application claims priority to and is a 35 U.S.C. §371 national stage entry of PCT/IL2008/001056, having an international filing date of Jul. 31, 2008 and claiming priority to U.S. Provisional Patent Application No. 60/963,045, filed on Aug. 1, 2007 and 60/999,654, filed on Oct. 19, 2007. The present application incorporates herein by reference the disclosures of each of the above-referenced applications in their entireties.

FIELD OF THE INVENTION

A system, device and a method for sustained medical infusion of fluids are described. Some embodiments relate generally to a miniature portable infusion device that can be attached to and detached from a patient's body and that is configured to accurately dispense fluids. Some embodiments relate to a skin securable infusion device that can be periodically disconnected from and reconnected to the body of the patient. Some embodiments relate to a skin securable infusion device that can be disconnected from and reconnected to the body and to a method for detecting whether the infusion device is disconnected or reconnected to the body and for controlling the device's operation accordingly.

BACKGROUND OF THE INVENTION

Medical treatment of several illnesses requires continuous drug infusion into various body compartments, such as subcutaneous and intra-venous injections. Diabetes mellitus patients, for example, require administration of varying amounts of insulin throughout the day to control their blood glucose levels. In recent years, ambulatory portable insulin infusion pumps have emerged as a superior alternative to multiple daily syringe injections of insulin. These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to individual prescription, since an overdose or under-dose of insulin could be fatal.

A first generation of portable infusion pumps refers to "pager-like" devices with a reservoir contained within the device's housing. In the first generation devices, a long tube delivers insulin from the pump, which is attached to a belt on the patient, to a remote insertion site. Such devices are disclosed, for example, in U.S. Pat. Nos. 3,771,694, 4,657,486 and 4,498,843. These devices represent a significant improvement over multiple daily injections, but nevertheless, they all suffer from several major drawbacks, among which are the large size and weight of the device, long tubing and lack of discreetness.

To avoid consequences associated with employing a long delivery tube, a new concept was proposed, which was implemented in second generation pumps. The second generation pumps concept relates to a remote controlled skin adherable device with a housing having a bottom surface adapted for contact with the patient's skin, a reservoir disposed within the housing, and an injection needle adapted for communication with the reservoir. This paradigm was described, for example, in U.S. Pat. Nos. 5,957,895, 6,589,229, 6,740,059, 6,723,072 and 6,485,461. The second generation devices also have several limitations: they are bulky, the remote control unit should always be at hand, and they are expensive because the entire device should be discarded every 2-3 days.

Third generation skin adherable devices were devised to avoid the cost issues of the second generation devices and to extend patient customization. An example of such a device was described in the co-owned, co-pending U.S. patent application Ser. No. 11/397,115 and co-owned International Application No. PCT/IL06/001276, the disclosures of which are incorporated herein by reference in their entireties. The third generation devices contain a remote control unit and a skin adherable patch unit (also referred to as a "dispensing patch unit") that includes two parts: (1) a reusable part containing driving and pumping mechanisms, electronics and other relatively expensive components, and (2) a disposable part containing a reservoir and, in some embodiments, batteries. A tube can also be provided which delivers the fluid from the reservoir to an outlet port that contains a connecting lumen.

This concept can provide a cost-effective skin adherable infusion device and allow diverse usage of the device, such as using it with various reservoir sizes, various needle and cannula types, etc.

In the co-pending, co-owned U.S. patent application Ser. No. 12/004,837, and co-owned International Patent Application No. PCT/IL07/001,578, both filed Dec. 20, 2007, and both claiming priority to U.S. Provisional Patent Application No. 60/876,679, filed Dec. 22, 2006, the disclosures of which are incorporated herein by reference in their entireties, a fourth generation patch unit that can be disconnected from and reconnected to a skin adherable cradle unit was disclosed. In the fourth generation the patch unit, after reservoir filling, is mounted on the body by the following steps:

1) Cradle unit is adhered to the skin;
2) Cannula is inserted through a cradle unit passageway (also referred to as a "well") into the subcutaneous tissue. The cannula, including a rubber septum, can be connected to the cradle unit's "well";
3) The patch unit is connected to the cradle unit. The connecting lumen pierces a rubber septum allowing fluid communication between the reservoir, cannula and the body.

In the co-pending, co-owned U.S. patent application Ser. No. 11/706,606, the disclosure of which is incorporated herein by reference in its entirety, a device containing a dispensing patch unit (called also "insulin dispensing patch") and an analyte sensing means (i.e., continuous glucose monitor) was disclosed. This dual function device is configured to have similar configuration to the one outlined above and can also be disconnected from and reconnected to a cradle unit upon patient discretion.

In some conventional systems, although basal delivery should be continuously administered, it is often interrupted due to periodic pump disconnection. In some situations, pump disconnection is mandatory, for example during sauna and hot bath because insulin cannot tolerate high temperatures. However, there are occasions in which a short time disconnection can substantially improve daily activity and patient satisfaction. If the operation of the patch unit's driving mechanism is not suspended prior to disconnection (for example, the user forgets to do so, the disconnection is unintentional, etc.), the patch unit will continue to dispense insulin even though it is not connected to the cradle unit, thus wasting precious insulin and battery power. Moreover, the patient's ability to control the precise amount of delivered insulin will be diminished.

SUMMARY OF THE INVENTION

An apparatus and a method for delivering a therapeutic fluid into a body of a patient are provided. In one aspect the device and the method can be implemented using a patch unit removably attachable to a cradle unit, said cradle unit removably attachable to the body of the patient; a position detector comprising a patch portion and a cradle portion, said patch portion coupled to the patch unit, said cradle portion coupled to the cradle unit; a processor adapted for receiving a position indication signal from the at least one position detector, said position indication signal corresponding to a physical proximity of the patch portion to the cradle portion; the processor is further adapted for receiving at least one command from the patient; and, wherein the portable therapeutic device is adapted for at least one therapeutic function selected from the group consisting of delivering a therapeutic fluid into the body of the patient and sensing a bodily analyte.

For example, the patch unit can comprise a reusable part and a disposable part; the disposable part can comprises a reservoir for storing the therapeutic fluid, and, the reusable part can comprise a metering portion for delivering the therapeutic fluid from said reservoir into the body of the patient. The patch unit can be configured to be remotely controlled. In some implementations, the therapeutic fluid can be insulin.

The processor can be adapted to control an operation of the patch unit based on the connection status signal received from the position detector. The processor can further be adapted to control the delivery of the therapeutic fluid into the patient based on the connection status signal. The processor can also be adapted to record commands received from the patient in a memory component. The processor is further adapted to deactivate at least one component of the apparatus based on the connection status signal received from the position detector. The processor can also be configured to initiate a notification to the patient, said notification corresponding to the connection status signal.

In some implementations, the cradle unit can have a cradle base configured as a flat sheet with an adhesive layer facing a skin of the patient and having anchoring means for connection and disconnection of said patch unit; and, a well configured to protrude upwardly from said cradle base to allow alignment and appropriate connection of said patch unit. For example, the well can be adapted for insertion of a cannula into the body of the patient.

In some implementations, the patch unit can be configured to use peristaltic pump to deliver the therapeutic fluid into the body of the patient. It can also be configured to use a piston to deliver the therapeutic fluid to the body of the patient.

In some implementations the position detector can comprise an optical sensor having a light source component and a light detector component. The position detector can also comprise an electro-magnetic detector and/or a magnetic proximity detector.

In another aspect, a method for activating a device for delivering a therapeutic fluid into a body can also be provided. For example, the method can comprise attaching a patch unit to a cradle unit; attaching the cradle unit to the body; generating an activation request for at least one component of at least one of the patch unit and the cradle unit based on a connection status signal generated by a position detector, said position detector comprising a patch portion and a cradle portion, the patch portion coupled to the patch unit, the cradle portion coupled to the cradle unit, said connection status signal corresponding to a physical proximity of the patch portion to the cradle portion.

A device is disclosed that can deliver therapeutic fluid into the body and/or monitor analyte concentration levels. For example, the device can include the following units:

A patch unit, which can be remotely controlled or manually controlled by operating buttons. In some embodiments, the patch unit can include two parts: reusable and disposable. The disposable part can be configured to include a reservoir and an outlet port with a connecting lumen. The reusable part can be configured to include electronics and at least a portion of a dispensing mechanism.

A cradle unit, which can be adherable to the patient's skin, e.g., by an adhesive.

After attaching the cradle unit to the skin, a cannula can be inserted into the subcutaneous compartment of the patient's body through a dedicated passageway ("well") provided in the cradle unit. During patch-cradle connection, the connecting lumen pierces a self-sealable rubber septum that seals the "well". Thus, fluid communication is established between the patch unit and the cannula. The patch unit can be connected to and disconnected from the cradle unit upon patient's discretion.

According to some embodiments, the device can be configured to include a position detector configured to detect whether the patch unit is connected to or disconnected from the cradle unit. The position detector, according to some embodiments, includes two parts, one of them being located on the patch unit ("patch portion") and the other on the cradle unit ("cradle portion"). A central processing unit ("CPU")/processor can be provided, which receives the position detector's output (connected/disconnected) and controls the patch unit's operation and fluid delivery, accordingly. For example, when the patch is disconnected, fluid delivery can be terminated and after reconnection, it can be resumed.

In some embodiments, the position detector's operation can be based on optical-type detectors or other means. For example, a light emitting diode ("LED") and a light detector can be adjacently located on the patch unit and the cradle unit can be provided with a reflective surface. Upon disconnection or reconnection, the CPU receives no/yes light inputs from the position detector and accordingly assigns the patch unit a "disconnected" or "connected" position status.

In some embodiments, the position detector is configured to operate as an electronic switch. For example, two conductive surfaces (in some embodiments, the surfaces can be fabricated from gold, nickel, or any other suitable material) can be attached to the lower surface of the patch unit's housing, and a third conductive surface can be attached to the cradle unit. The CPU is configured to assign the patch a certain position status according to whether the patch-cradle conductive surfaces are connected or disconnected ("ON-OFF" state).

Some embodiments include a device that includes a dispensing and/or sensing patch unit that can be disconnected from and reconnected to a skin adherable cradle unit, and that further includes a position detector, while the operation of the device can be controlled according to position detection.

Some embodiments include a device that can includes a miniature patch unit that can be configured to continuously dispense insulin and/or monitor glucose levels, and that further incorporates a position detector, and whose operation can be controlled according to position detection.

Some embodiments include a patch unit that can be disconnected from and reconnected to a cradle unit and enables users to safely disconnect the patch unit for a certain period of time.

Some embodiments include a device that includes a patch unit that can be remotely controlled and can be disconnected from and reconnected to a skin adherable cradle unit and that includes a position detector, and whose operation can be controlled according to position detection.

Some embodiments include a device that includes a patch unit having two parts, e.g., a reusable part and a disposable part, and that can be disconnected from and reconnected to a skin adherable cradle unit, and that further includes a position detector, and whose operation can be controlled according to position detection.

Some embodiments include a device which is miniature, discreet, economical for the users and highly cost effective for the payer, and that incorporates a position detector, and whose operation can be controlled according to position detection.

Some embodiments include a patch unit that continuously monitors body glucose (e.g., blood, ISF) levels and can concomitantly deliver insulin into the body, and that incorporates a position detector, and whose operation can be controlled according to position detection.

Some embodiments include a semi closed-loop system that monitors glucose levels and dispenses insulin according to sensed glucose levels, and incorporates a position detector and operation of the device can be controlled according to position detection.

Some embodiments describe a device that includes a dispensing and/or sensing patch unit (hereinafter, referred to generally as a "patch" or a "patch unit") that can be disconnected from and reconnected to a skin adherable cradle unit, and that includes a detector device that is configured to detect whether the patch is connected or disconnected (hereinafter, referred to as "position detector"). It is also desirable to provide a method for controlling patch operation according to a position of the patch that has been detected by the position detector.

It is desirable to provide a device that includes a miniature patch that can continuously dispense insulin and/or monitor glucose levels and incorporates a position detector and its operation is controlled according to position detection.

It is also desirable to provide a dispensing patch that can be disconnected from and reconnected to a cradle unit and that enables users to safely disconnect the patch unit for a period of time.

It is desirable to provide a device that contains a patch unit that can be remotely controlled and can be disconnected from and reconnected to a skin adherable cradle unit and that further includes a position detector, whose operation can be controlled according to position detection.

It is desirable to provide a device that contains a patch unit, which includes two parts, e.g., a reusable part and a disposable part, and which can be disconnected from and reconnected to a skin adherable cradle unit, and incorporates a position detector, whose operation can be controlled according to position detection.

It is desirable to provide a device that is miniature, discreet, economical for the users, and cost effective for the payer and that incorporates a position detector, whose operation can be controlled according to position detection.

It is desirable to provide a device that can continuously monitor body glucose (e.g. blood glucose, ISF glucose) levels and concomitantly deliver insulin into the body, and that incorporates a position detector, while the operation of the device can be controlled according to position detection.

It is desirable to provide a device that constitutes a semi closed-loop system that monitors glucose levels and dispenses insulin according to sensed glucose levels, and that incorporates a position detector, while the operation of the device can be controlled according to position detection.

The foregoing and other features, aspects, and advantages of the present invention will be more apparent from the following detailed description, which illustrates exemplary embodiments of the present invention.

DETAILED DESCRIPTION OF THE INVENTION

Figure 1A:
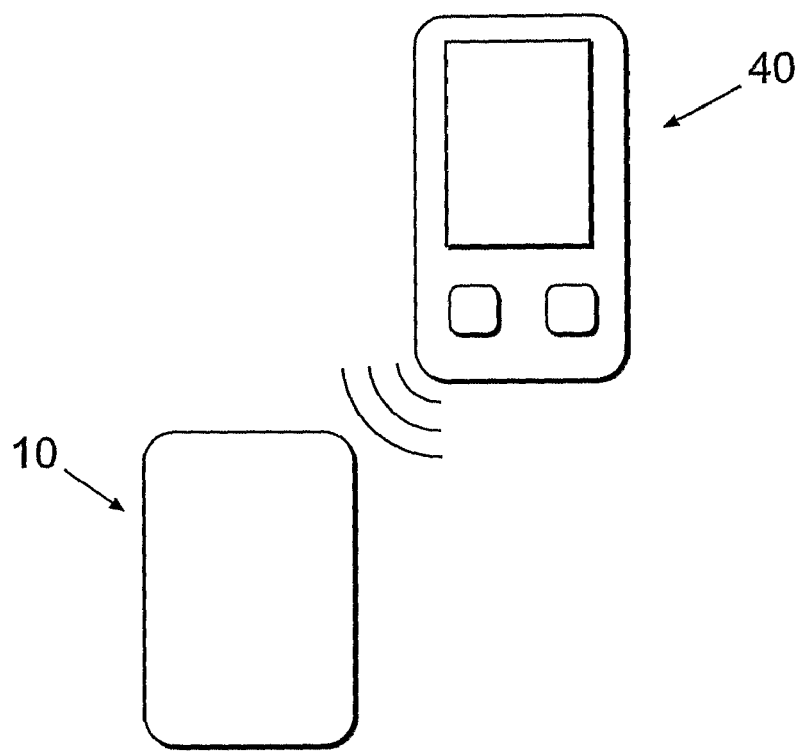
FIGS. 1a-b illustrate an exemplary device having a patch unit and a remote control unit.
Figure 1B:
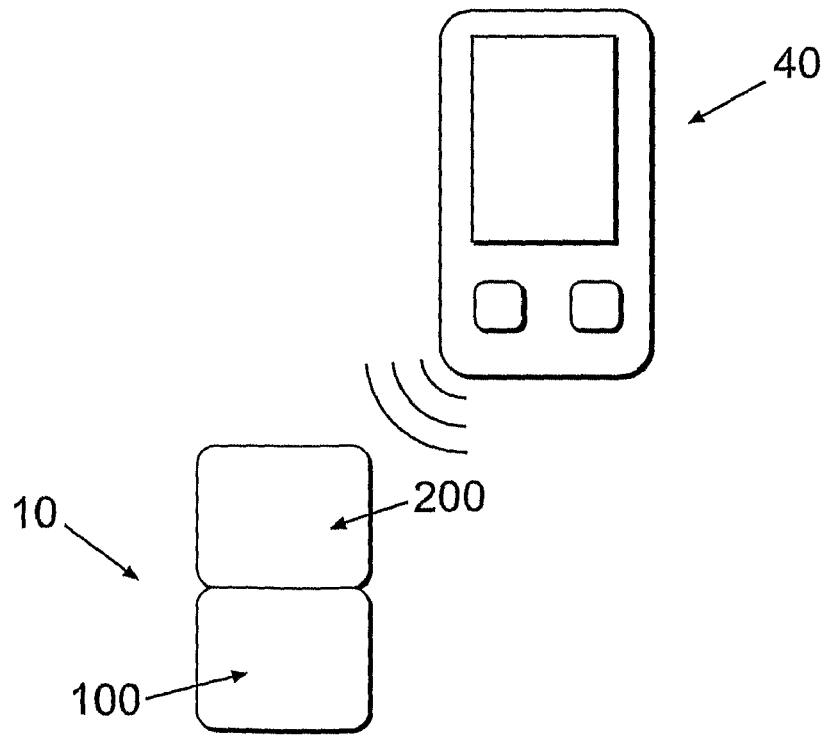

FIGS. 1a-b illustrate a device having a patch unit (10) capable of dispensing and/or sensing (hereinafter referred to generally as "patch" or "patch unit") and a remote control unit (40). In some embodiments, the patch unit (10) can include a single part (FIG. 1a) or two parts (FIG. 1b), e.g., reusable part (100) and disposable part (200).

In some embodiments, fluid delivery can be programmed solely by the remote control unit (40) and/or by manual buttons (not shown) which could be provided on the patch unit (10). An embodiment of this arrangement is disclosed in our co-owned International Patent Application No. PCT/IL08/001,001, filed Jul. 20, 2008, claiming priority to U.S. Provisional Patent Application No. 60/961,527, filed Jul. 20, 2007, and titled "Manually Operable Portable Infusion Device", the disclosures of which are incorporated herein by reference in their entireties.

Figure 2A:
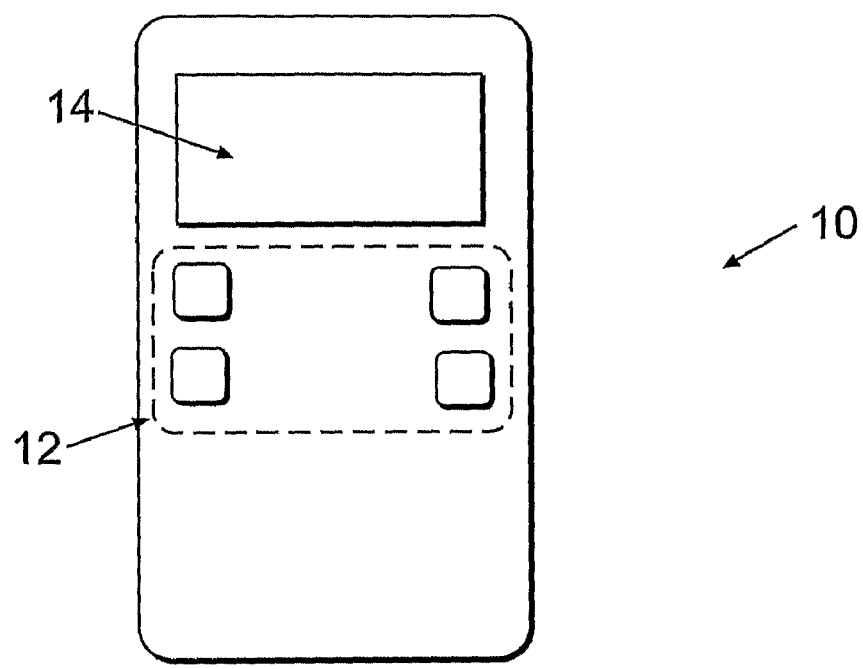
FIGS. 2a-b illustrate an exemplary device having a patch unit provided with operating buttons and a display.
Figure 2B:
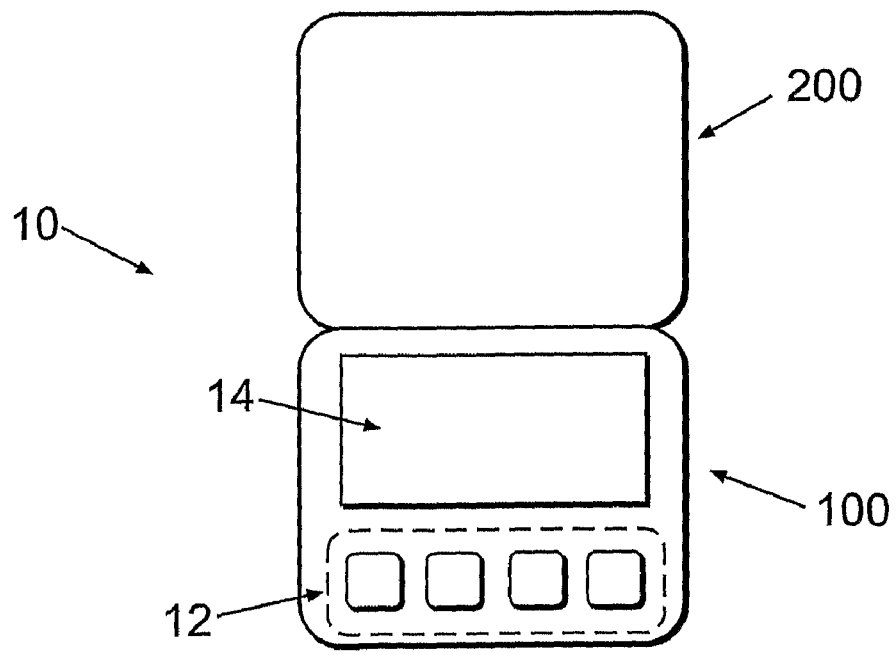

FIGS. 2a-b illustrate another embodiment of the device having a patch unit (10) provided with operating buttons (12) (e.g., keypad) and a display (14). In some embodiments, fluid delivery programming can be carried out by the operating buttons (12). In other embodiments, the device can include also a remote control unit. The patch unit (10) can include a single part (FIG. 2a) or two parts (FIG. 2b), e.g., reusable part (100) and disposable part (200). In these embodiments, the operating buttons (12) and the display (14) can be located on the reusable part (100). An embodiment of this arrangement is disclosed in a co-owned, International Patent Application No. PCT/IL08/001,057, entitled "Portable Infusion Device with Means for Monitoring and Controlling Fluid Delivery", filed on Jul. 31, 2008, claiming priority to U.S. Provisional Patent Applications No. 60/963,148, filed Aug. 1, 2007, and No. 61/004,019, filed Nov. 21, 2007, both entitled "Portable Infusion Device with Means for Monitoring and Controlling Fluid Delivery", the disclosures of which are incorporated herein by reference in their entireties.

In some embodiments, the device can include a cradle unit (20) that can be adhered to the skin of the patient, so that the patch unit (10) can be connected to and/or disconnected from the cradle unit (20) as desired. An embodiment of the device employing the cradle unit is disclosed in co-owned U.S. patent application Ser. No. 12/004,837, and International Patent Application No. PCT/IL07/001,578, both filed Dec. 20, 2007, and both claiming priority to U.S. Provisional Patent Application No. 60/876,679, filed Dec. 22, 2006, the disclosures of which are incorporated herein by reference in their entireties.

Figure 3A:
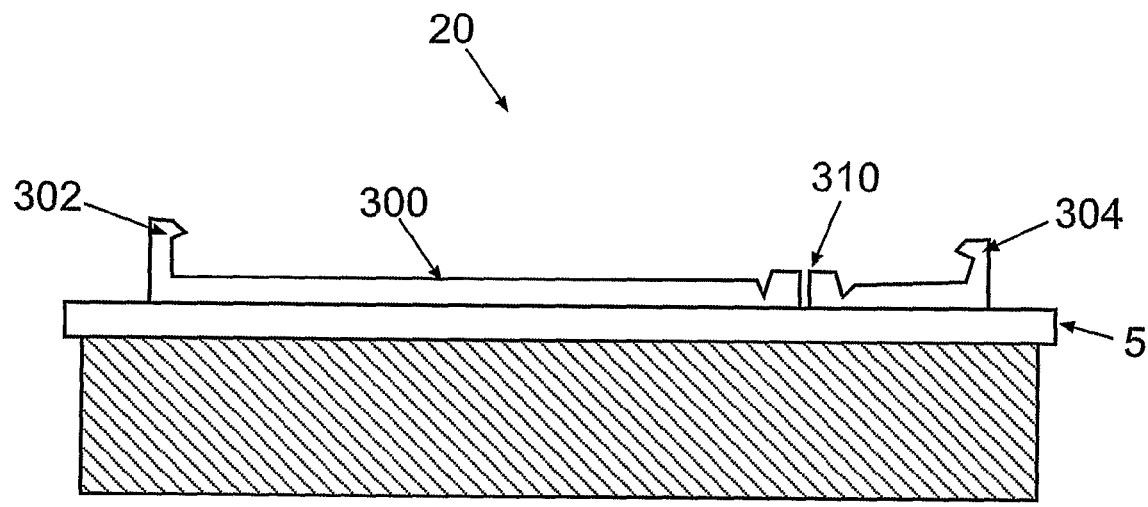
FIGS. 3a-c illustrate an exemplary cradle unit having a cradle base and a well.
Figure 3B:
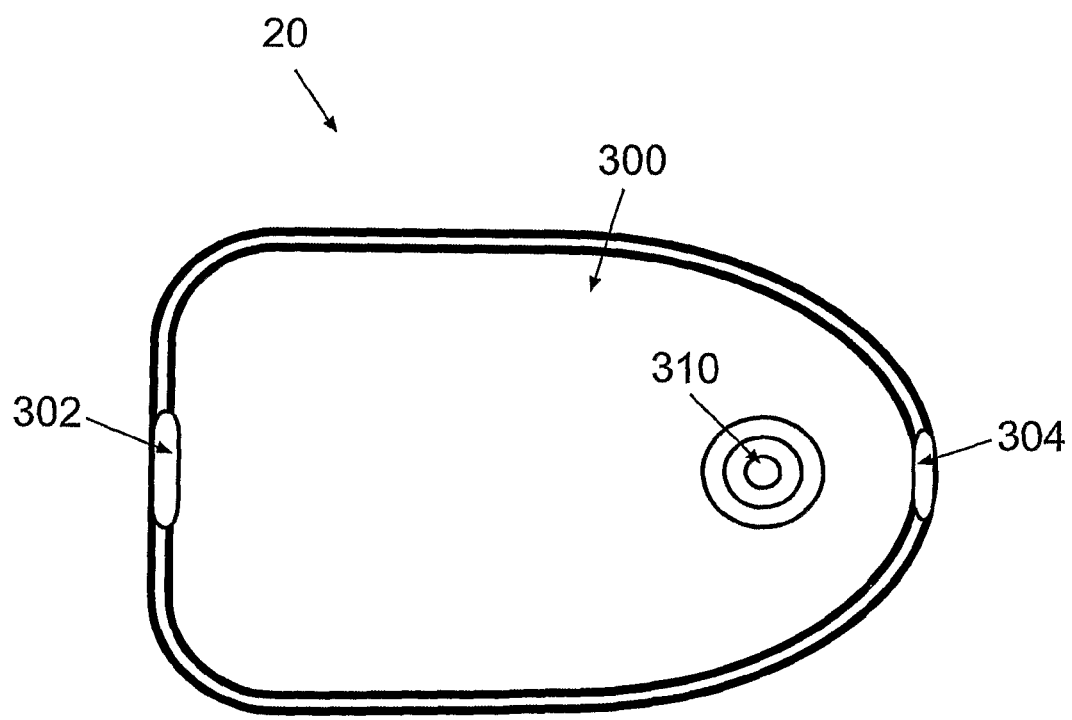

FIGS. 3a-b illustrate side and upper views (respectively) of an exemplary cradle unit (20). The cradle unit (20) can include the following elements:

Cradle base (300)—configured as a flat sheet with an adhesive layer facing the skin (5) and with anchoring latches (302, 304) on its upper side for connection and disconnection of the patch unit.

Well (310)—configured as a tubular protrusion emerging upwardly from the cradle base (300) to allow alignment with and appropriate connection of the patch unit. The well (310) constitutes a passageway through which a cannula (not shown) can be inserted into the patient's body for fluid (e.g. insulin) delivery and/or for analyte (e.g. glucose) sensing. The cradle unit (20) can be configured to have more than one "well". For example, in case when two cannulae are employed, one for fluid delivery and the other for analyte sensing.

Figure 3C:
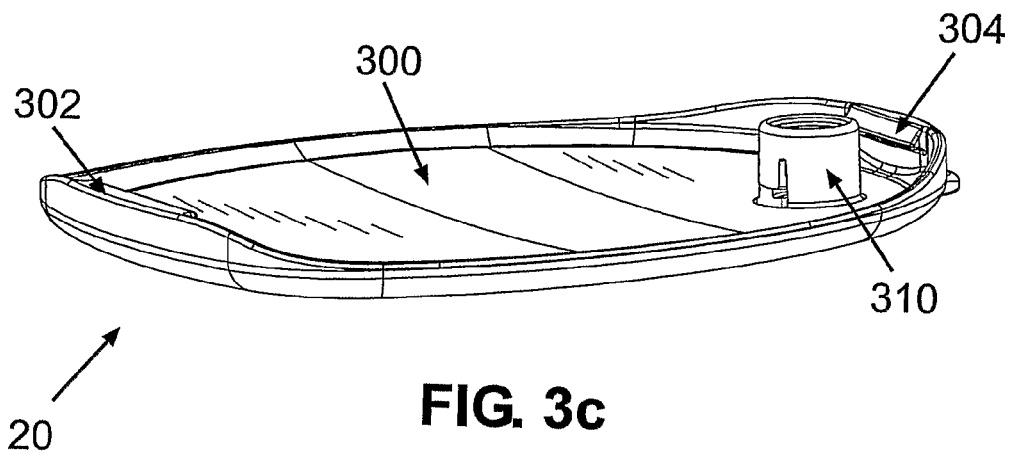

FIG. 3c illustrates an exemplary embodiment of the cradle unit (20) having a cradle base (300) with anchoring latches (302, 304) and a well (310). Upon attachment of the cradle unit (20) to the patient's skin (5), a cannula (not shown) can be inserted into the subcutaneous compartment of the patient's body through the well (310) of the cradle unit (20). The insertion of the cannula into the subcutaneous compartment can be carried out by a dedicated inserter (not shown), e.g., an embodiment of which is disclosed in a co-owned International Patent Application No. PCT/IL08/000,859 and co-owned, co-pending U.S. patent application Ser. No. 12/215,219, filed Jun. 25, 2008, claiming priority to U.S. Provisional Patent Application No. 60/937,155, entitled "Protector for Cannula and Penetrating Member Insertable in the Body of a Patient", and filed Jun. 25, 2007, and co-owned International Patent Application No. PCT/IL08/000,860 and co-owned, co-pending U.S. patent application Ser. No. 12/215,255, filed Jun. 25, 2008, claiming priority to U.S. Provisional Patent Application No. 60/937,214, entitled "Insertion Device for Inserting a Cannula into a Body", and filed Jun. 25, 2007, disclosures of which are incorporated herein by reference in their entireties. Following cannula insertion, a patch unit can be connected to the cradle unit, and fluid delivery and/or analyte sensing can be established.

Figure 4A:
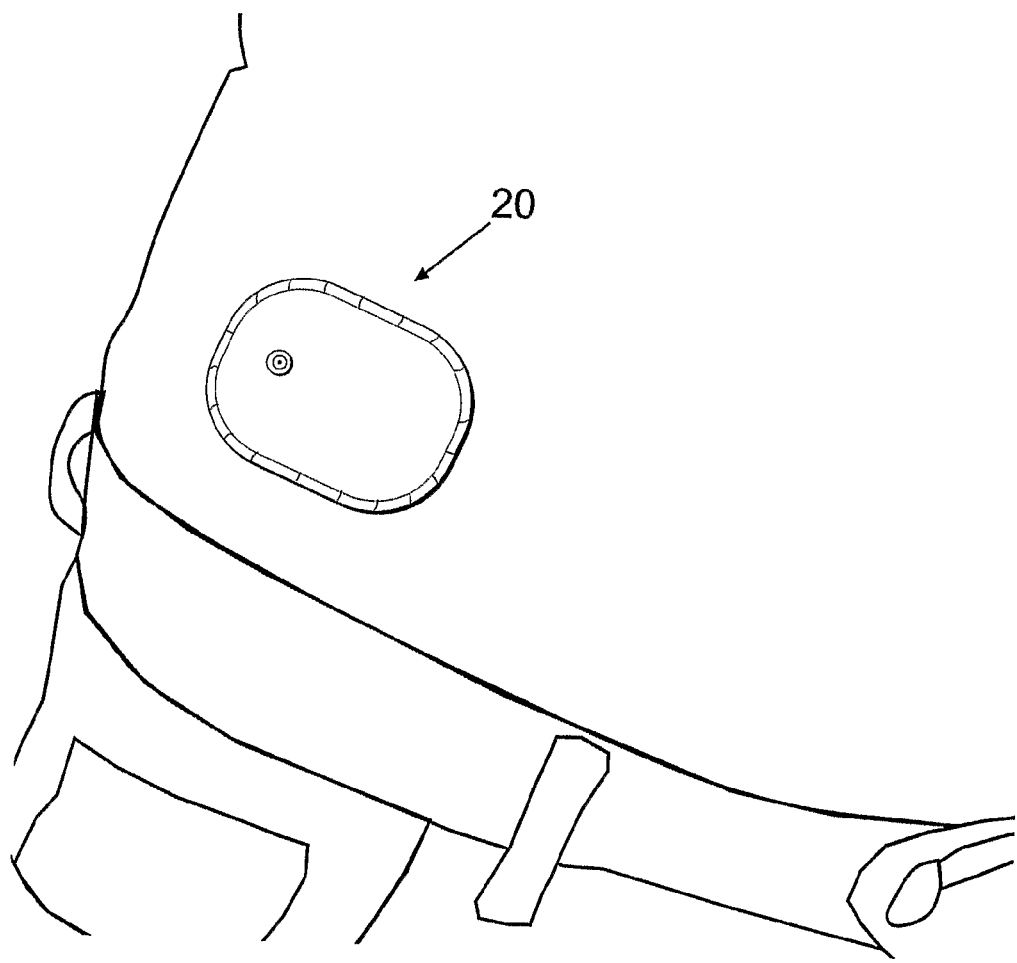
FIGS. 4a-d illustrate an exemplary connection of a patch unit to a skin adherable cradle unit.
Figure 4B:
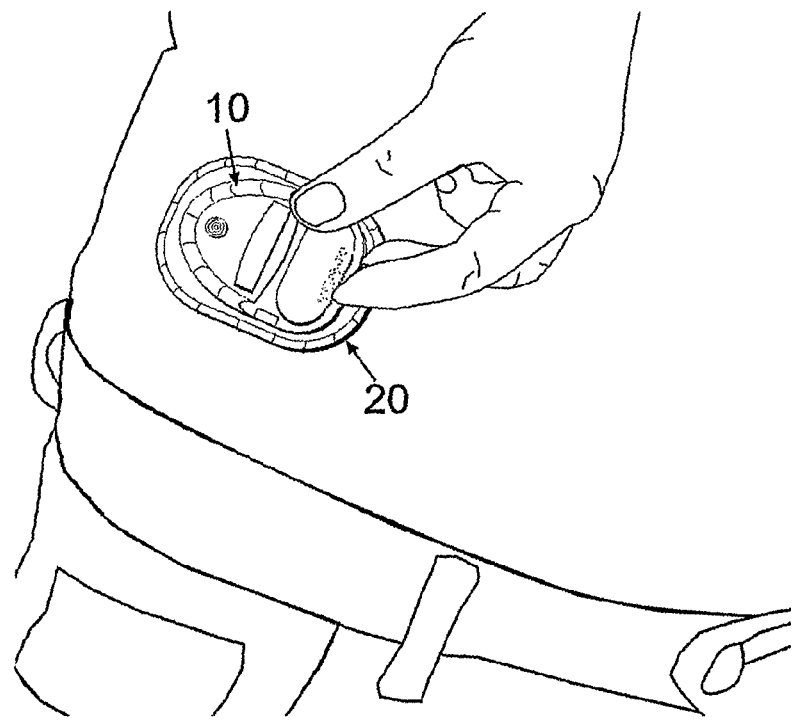
Figure 4C:
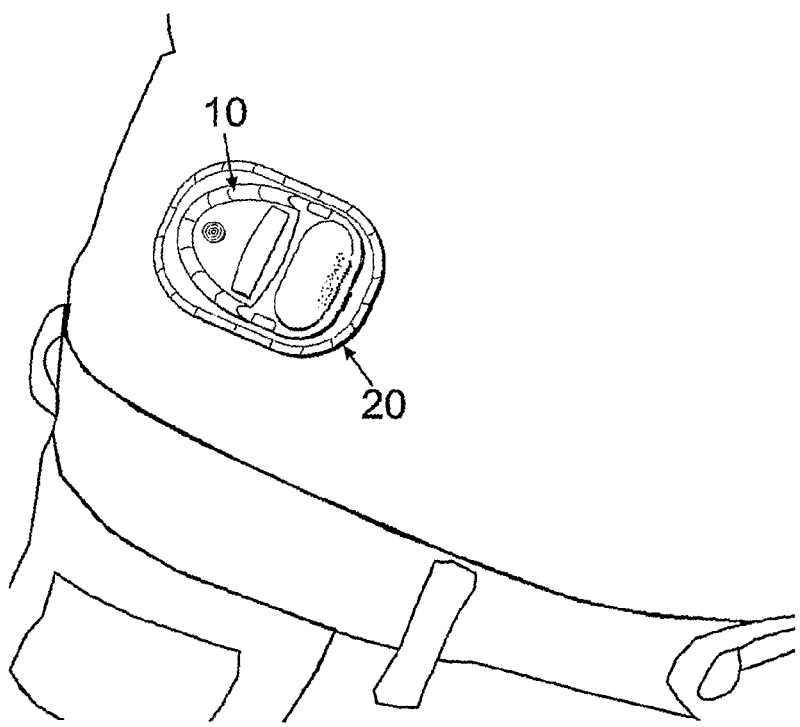
Figure 4D:
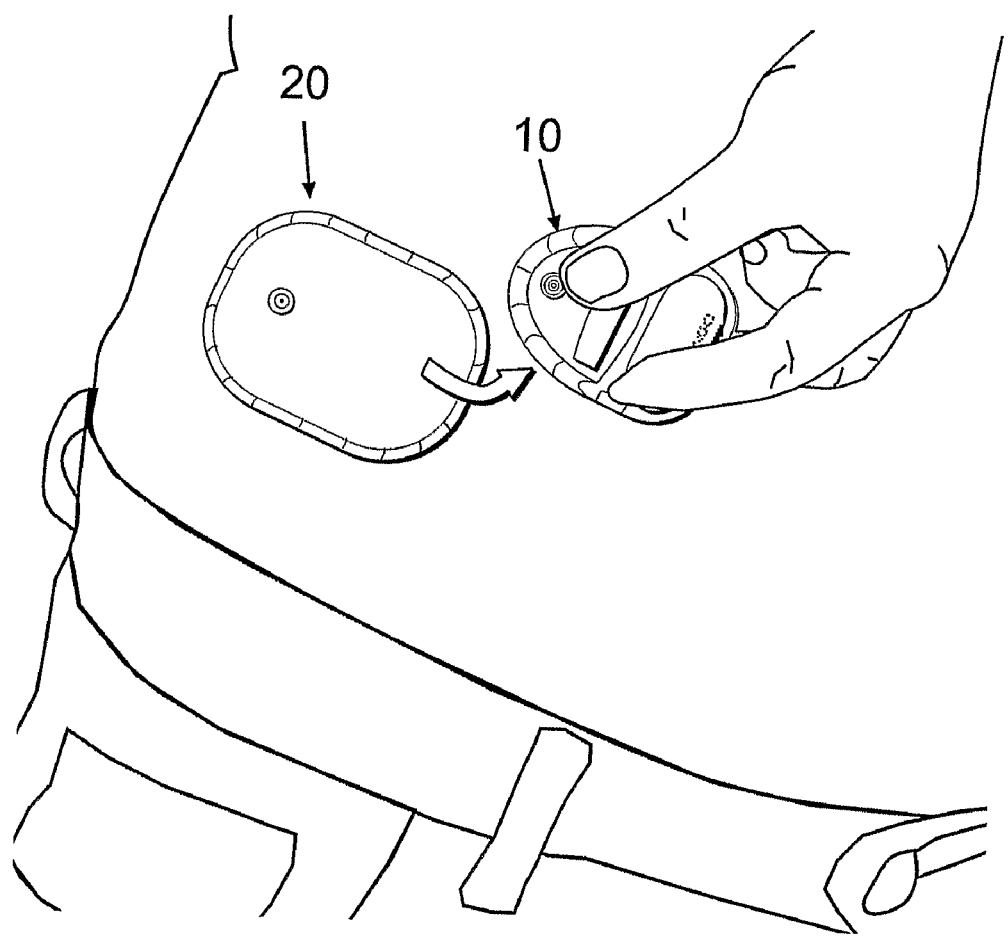

FIG. 4a illustrates the cradle unit (20) being adhered to the patient's skin (5). FIG. 4b illustrates an exemplary connection of the patch unit (10) to the adhered cradle unit (20) (after cannula insertion). FIG. 4c illustrates the patch unit (10) being connected to the cradle unit (20) and ready for operation. FIG. 4d illustrate the patch unit (10) being disconnected from the cradle unit (20).

Figure 5A:
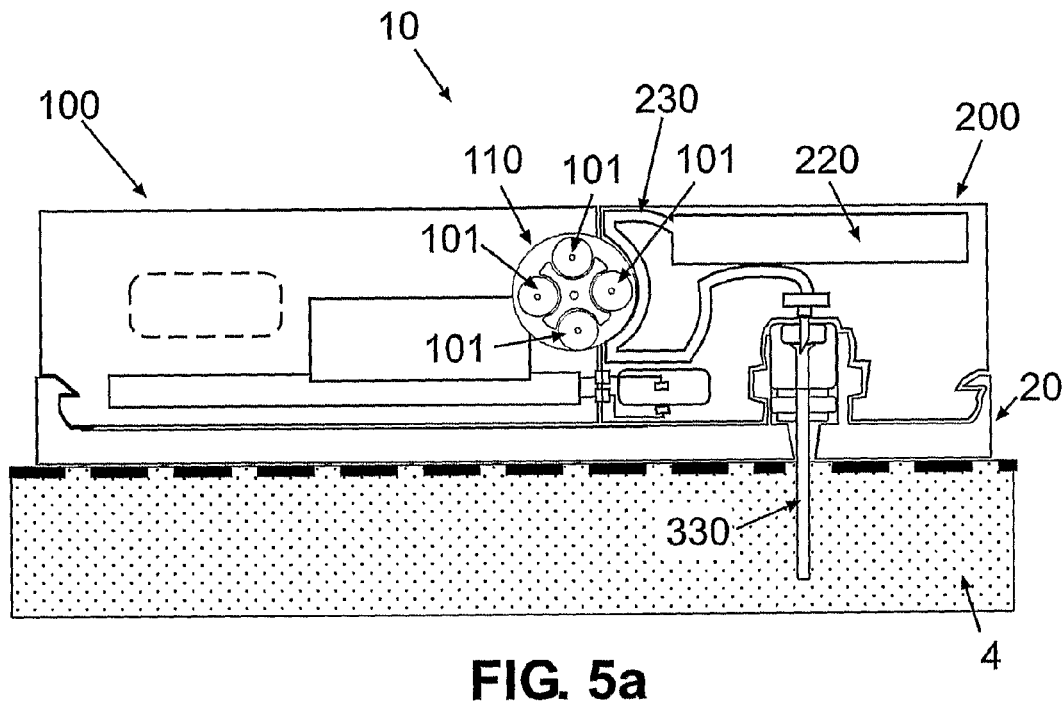
FIGS. 5a-d illustrate exemplary patch units that can be configured to be connected to a skin adherable cradle unit.
Figure 5B:
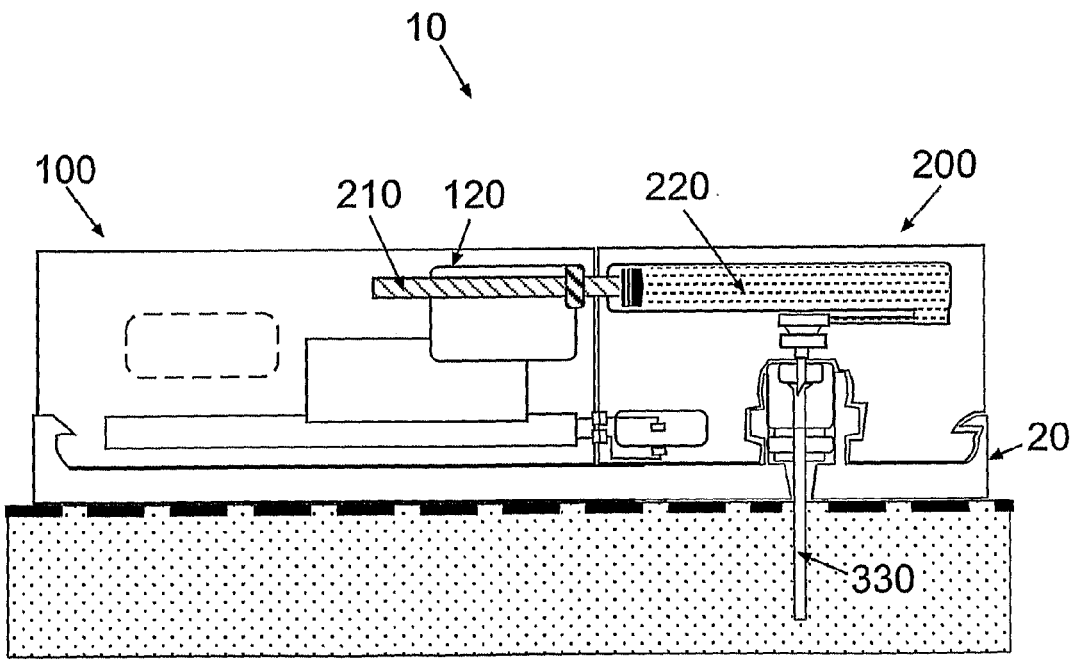
Figure 5C:
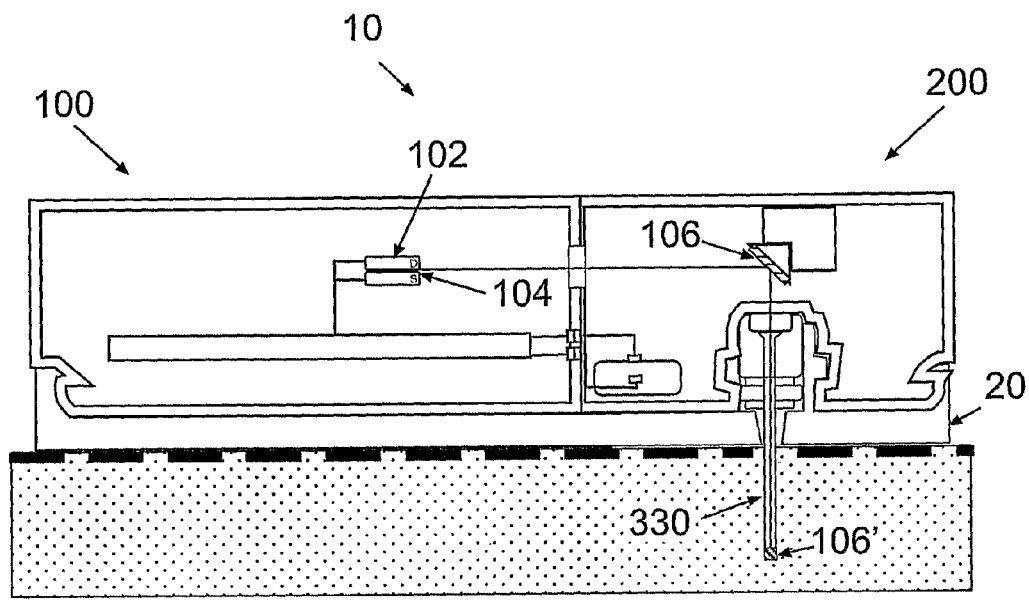
Figure 5D:
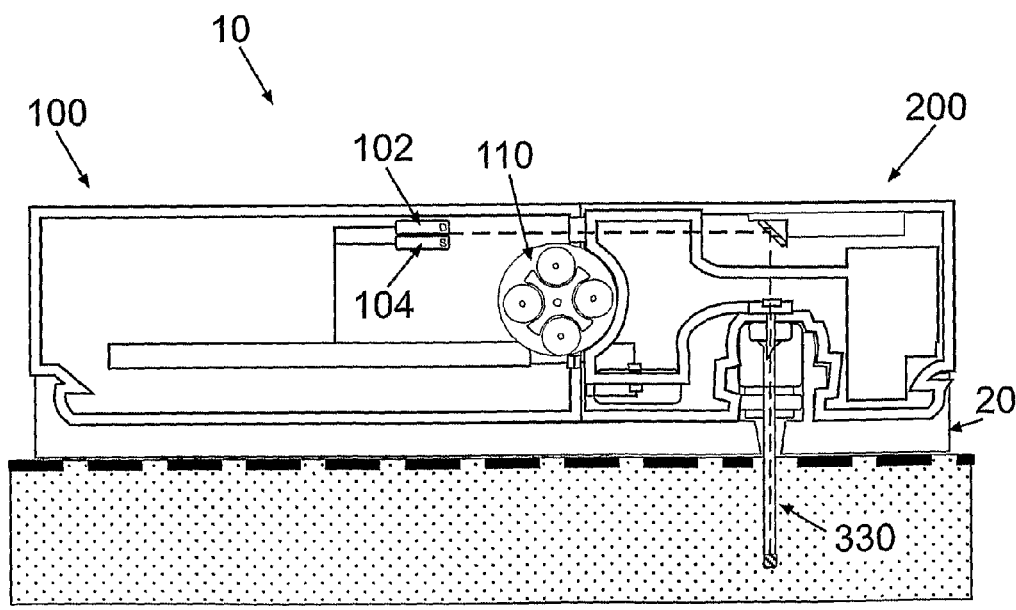

FIGS. 5a-d illustrate exemplary patch units that are configured to be attached to the cradle unit (20). FIG. 5a illustrates an exemplary fluid delivery device having a cradle unit (20) and a two-part dispensing patch unit (10) that employs a peristaltic pumping mechanism. Rotation of a rotary wheel (110) and pressing of rollers (101) against a delivery tube (230) periodically positively displaces fluid from a reservoir (220) into the delivery tube (230) by virtue of a peristaltic motion. The fluid is then delivered via a cannula (330) into the subcutaneous compartment (4) within the patient's body. An exemplary two-part dispensing patch unit employing a peristaltic pumping mechanism is disclosed in co-pending, co-owned U.S. patent application Ser. No. 11/397,115 and co-owned International Application No. PCT/IL06/001276, the disclosures of which are incorporated herein by reference in their entireties. FIG. 5b illustrates an exemplary fluid delivery device having a cradle unit (20) and a two-part dispensing patch unit (10), which employs instead of a peristaltic pumping mechanism a syringe-type pumping mechanism. A plunger (210) is displaced within a reservoir (220) and forces fluid towards the cannula (330). An exemplary embodiment of this arrangement is disclosed in a co-owned, International Patent Application No. PCT/IL08/000,641, filed May 11, 2008, claiming priority to U.S. Provisional Patent Application No. 60/928,815, filed May 11, 2007, the disclosures of which are incorporated herein by reference in their entireties. FIG. 5c illustrates an exemplary analyte sensing device having a two-part sensing patch unit (10) and a cradle unit (20). In an embodiment of FIG. 5c, an optical sensor for analyte sensing can be employed. One or more optical means (106, 106') (e.g., reflectors) can be used for creating an optical path between a light source (102) and a sample. In some embodiments, the optical path can be located in the subcutaneous portion of the cannula (330). In some embodiments, the optical path terminates at a light detector (104). An embodiment of this arrangement is disclosed in co-owned, co-pending U.S. patent application Ser. No. 11/989,678, filed Jan. 28, 2008, and co-owned International Patent Application No. PCT/IL07/001,096, filed Sep. 5, 2007, both claiming priority to U.S. Provisional Patent Application No. 60/842,869, filed Sep. 6, 2006, and U.S. patent application Ser. No. 11/989,665, filed Jan. 28, 2008 and International Patent Application No. PCT/IL07/001,177, filed Sep. 25, 2007, both claiming priority to No. 60/848,511, filed Sep. 29, 2006, the disclosures of which are incorporated herein by reference in their entireties. FIG. 5d illustrates an exemplary dual function device having a cradle unit (20) and a patch unit (10) that can be configured to dispense therapeutic fluid (e.g., insulin) and sense analyte (e.g. glucose). This device can be configured to employ a single cannula shared for both fluid delivery and analyte sensing. The dispensing and sensing functions can be independent from one another, or as an alternative, the device may operate in a semi or fully closed-loop mode. An embodiment of this arrangement is disclosed in a co-pending, co-owned U.S. patent application Ser. No. 11/706,606, the disclosure of which is incorporated herein by reference in its entirety.

Although basal delivery can be continuously administered to the patient, nevertheless in practice it is often interrupted due to periodic patch unit disconnections, whether mandatory (e.g., during sauna and hot bath), voluntary (e.g., when going to the beach), or accidentally. According to some embodiments, a dedicated position detector can be provided within the device for detecting whether the patch unit is connected or disconnected. For example, the position detector can be configured to generate a signal output, which can be received at the central processing unit (CPU). The position detector's signal output can correspond to the current position status of the patch unit, i.e., whether it is connected to the cradle unit or disconnected therefrom. Upon receiving the output signal, the CPU can assign the patch unit the appropriate position status. Some embodiments implement a method for controlling the patch unit's operation according to the position status of the patch unit assigned by the CPU upon receiving the position detector's signal output.

The position detector according to some embodiments comprises two parts one of which being located on the patch unit ("patch portion") and the other on the cradle unit ("cradle portion"). It should be borne in mind that according to other embodiments the position detector may comprise only a single part.

Figure 6A:
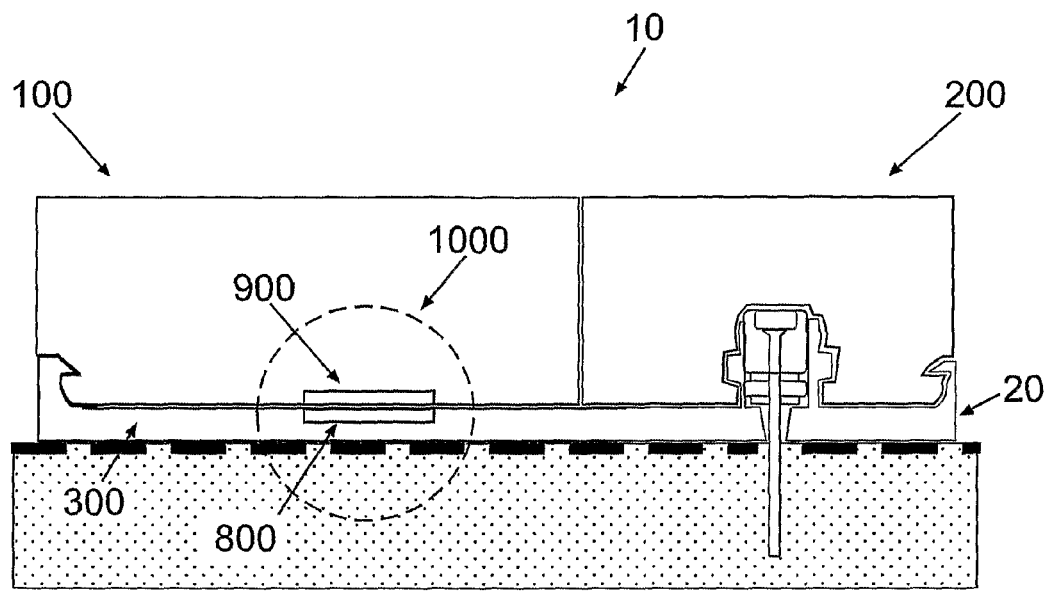
FIGS. 6a-c illustrate various optional locations of a two-part position detector.
Figure 6B:
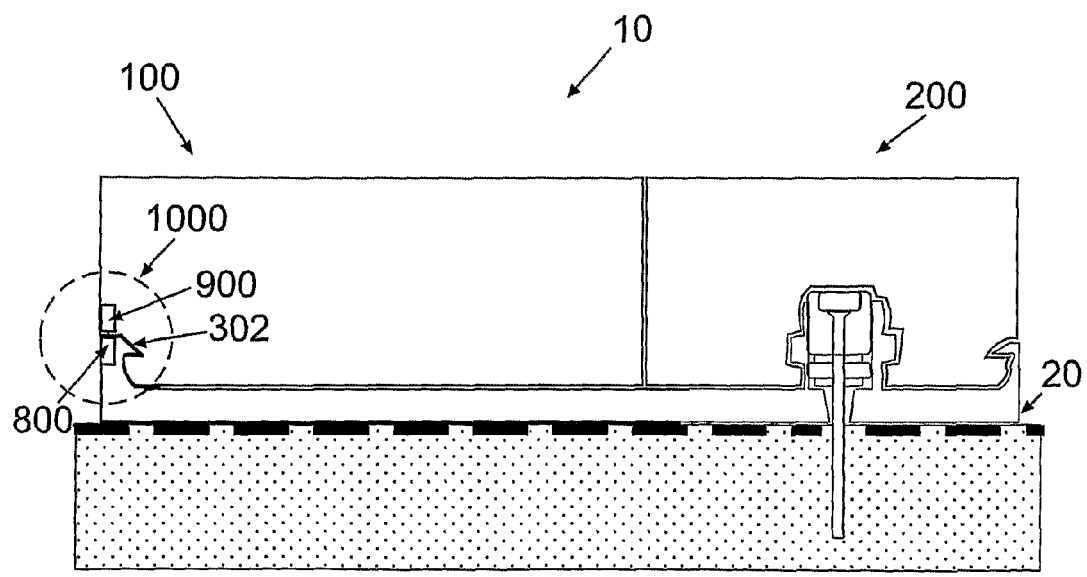
Figure 6C:
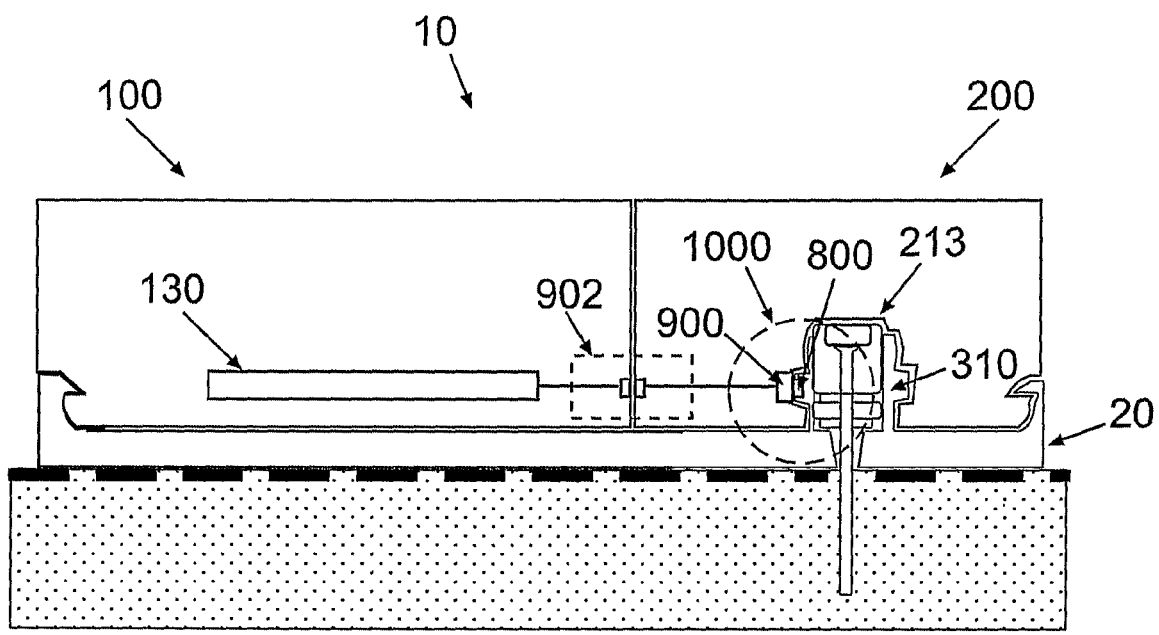

FIGS. 6a-c illustrate various locations of parts of a position detector (1000) on the cradle unit (20) and on the patch unit (10). FIG. 6a illustrates an embodiment in which one part, namely a cradle portion (800), is located on the upper side of a cradle base (300) while the other part, namely a patch portion (900), is located on the bottom side of the patch unit (10). In case of a two-part patch unit (10), the patch portion (900) can be located on the reusable part (100). However, the patch portion (900) can be located on the disposable part (200) as well. When the patch portion is located on the reusable part, a printed circuit board ("PCB") can be used for electrical connection of the patch portion to the CPU. In some embodiments, the PCB can be made available in the reusable part. When the patch portion is located on the disposable part, a dedicated electrical means (e.g., wires, metal tabs, etc.) can be used to electrically connect the patch portion to the PCB. FIG. 6b illustrates an exemplary embodiment in which the cradle portion (800) of the position detector (1000) is located on one of the cradle unit's anchoring latches (e.g., on the latch designated by numeral 302) and the patch portion (900) of the position detector (1000) is located in close proximity. FIG. 6c illustrates an exemplary embodiment in which the cradle portion (800) of the position detector (1000) is located on the well (310) and the patch portion (900) of the position detector (1000) is located on the patch unit's outlet port (213). In some embodiments, where the patch unit (10) includes two parts, the outlet port (213) could be located in the disposable part (200), and, thus, the patch portion (900) will be provided with dedicated means (902) (e.g. wires, metal tabs) for electrical connection to the PCB (130) located in the reusable part (100).

Figure 7:
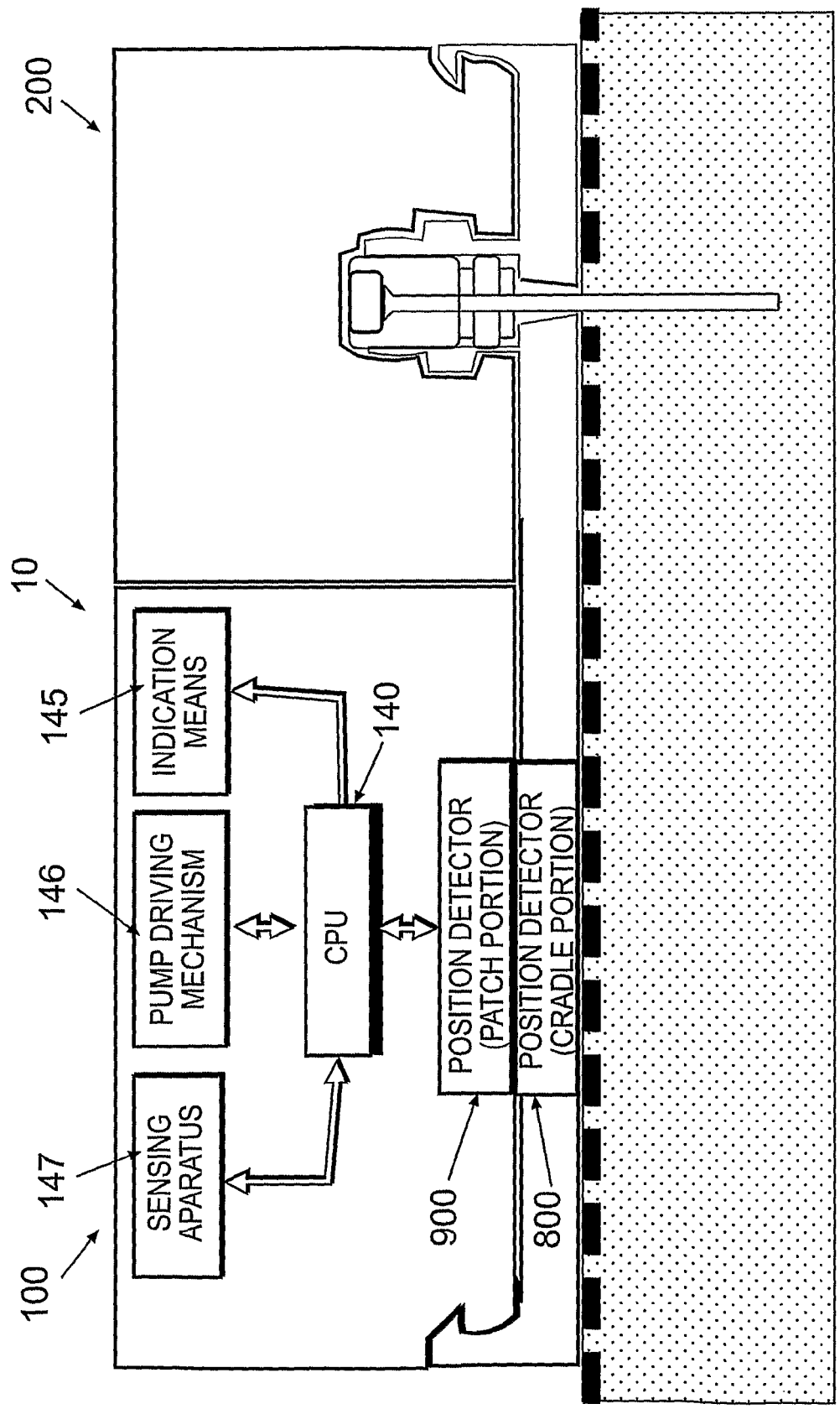
FIG. 7 illustrates an exemplary scheme of the components associated with the patch unit's position status setting and operation control.

FIG. 7 illustrates exemplary components associated with the patch unit's position status setting and operation control. The output of the position detector's patch portion (900), which, in the embodiment of FIG. 7 can be located in the reusable part (100), is received at the CPU (140). The CPU (140) can assign the patch unit a "connected" or "disconnected" position status according to received output, and then control the operation of the pump driving mechanism (146) and/or sensing apparatus (147) according to the detected patch unit position status (e.g., deactivation of pump driving mechanism (146) and/or sensing apparatus (147) when the patch unit is disconnected from the cradle unit (20)). The CPU (140) can be configured to notify the user via an indication means (145) for indicating the current position status.

FIGS. 8-12 illustrate exemplary cross-sectional views of a two-part patch unit (10) and a cradle unit (40) employing various types of position detectors. For illustrative purposes only, in the figures the cradle portion of the position detector is located on the upper side of the cradle base (300) and the patch portion of the position detector on the patch unit's (10) bottom side. As can be understood by one skilled in the art, both detector portions can be located adjacently at any other location of patch and cradle units.

Figure 8A:
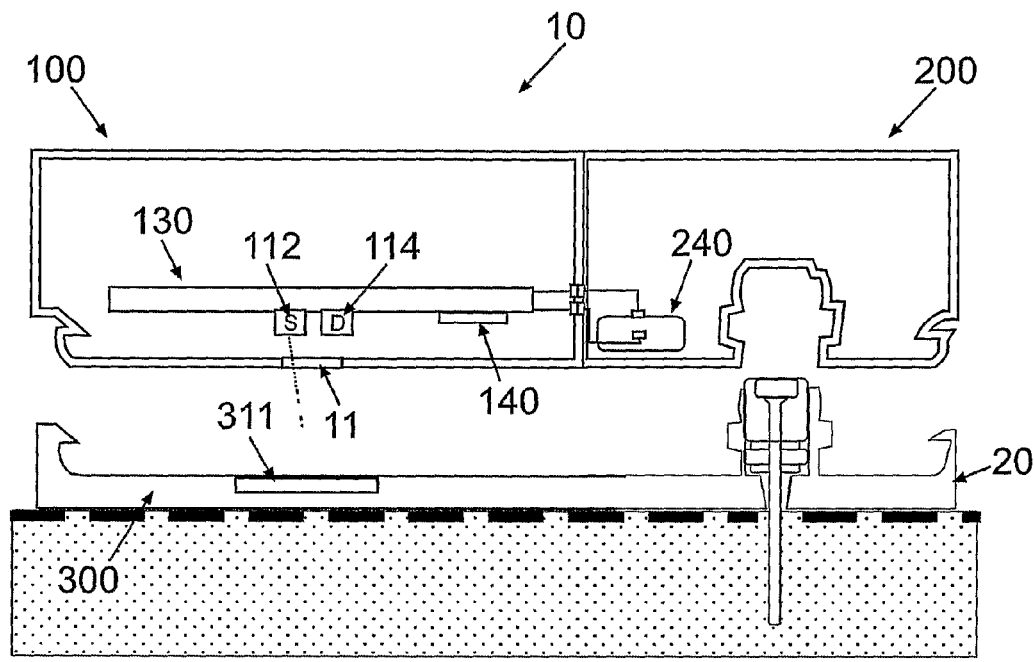
FIGS. 8a-c and 9a-b illustrate exemplary optical position detectors.
Figure 8B:
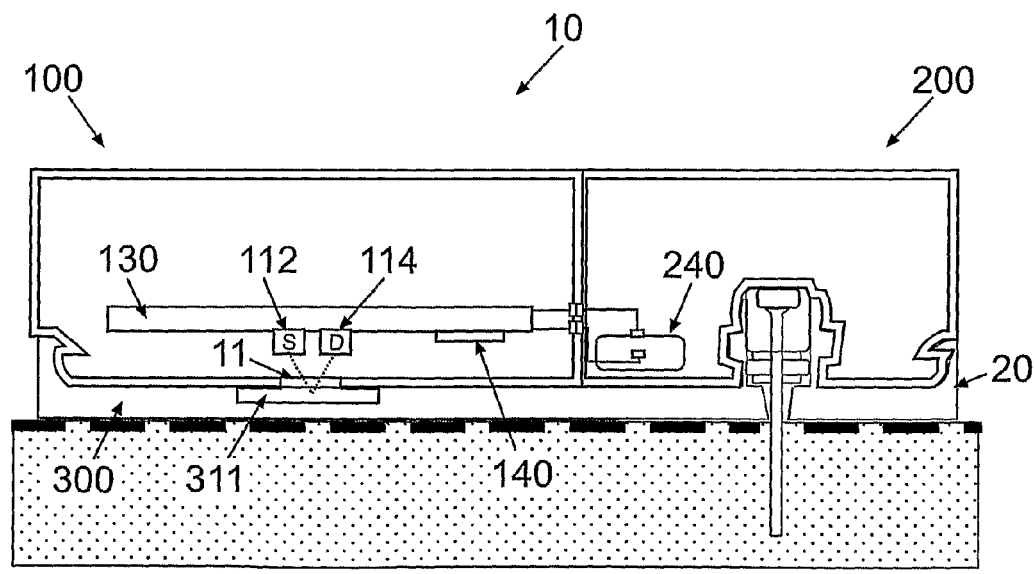
Figure 8C:
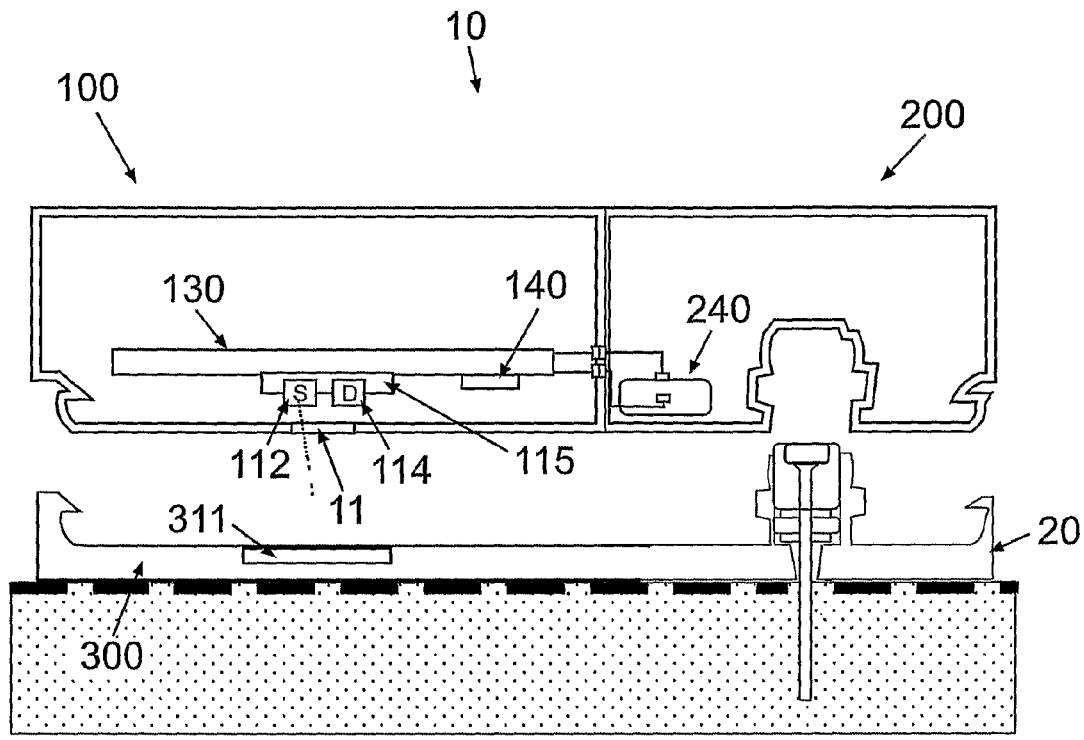

FIGS. 8a-c illustrate an embodiment of a position detector that can be configured to use optical sensing. In this embodiment, the position detector can be configured to include a light emitting diode (LED) (112) and a light detector (114). The LED (112) and light detector (114) are configured to be adjacent to the bottom side of the PCB (130) (e.g., the side of the PCB (130) that faces the cradle unit (20)). The LED (112) and the light detector (114) may be separately located items, as shown in FIGS. 8a-b, or they may be fixed adjacent to each other being deployed on a common support frame (115), as shown in FIG. 8c. The LED (112) and the light detector (114) can be configured to have leads (not shown), which can be soldered to the PCB (130), thereby establishing electrical connection. In some embodiments, at least a portion (11) of the housing of the reusable part (100), which is located beneath, the LED (112) and the light detector (114), can be fabricated from a transparent material so that light could pass through it. The cradle base (300) can be provided with a reflective surface (311), which is located opposite to the transparent portion (11) of the reusable part (100) housing. The reflective surface (311) can be embedded in the cradle base (300) or alternatively it can protrude from the cradle base (300). FIG. 8a illustrates exemplary patch unit (10) and cradle unit (20), when they are not connected. In this case the light emitted by the LED (112) passes through the transparent portion (11) of the reusable part's housing and it is not sensed by the light detector (114). FIG. 8b illustrates exemplary patch unit (10) being connected to the cradle unit (20). The light emitted by the LED (112) passes through the transparent portion (11) of the reusable part (100) housing, is reflected by the reflective surface (311) of the cradle unit (20), and is then sensed by the light detector (114). It will be noted that in case the cradle unit (20) is transparent, the patient's skin may act as a reflective surface, in which case the transparent configuration of the cradle unit can act as the cradle unit portion of the position detector. In some implementations, the cradle unit (20) can be fabricated entirely from a reflective material, or it can be painted in a bright color. In these cases, the reflective qualities of the cradle unit can represent the cradle portion of the position detector.

The CPU (140) is configured to receive "yes"/"no" light detection signals, set the patch unit's position status to "connected" or "disconnected" based on the received signal, and control the patch unit's operation accordingly.

The LED (112) can be configured to emit light continuously, periodically (e.g. every 1 sec for a period of 1 µsec), or in any other fashion. This can be done to save energy supplied by at least one battery (240) located in the disposable part (200) or in the reusable part (100).

Figure 9A:
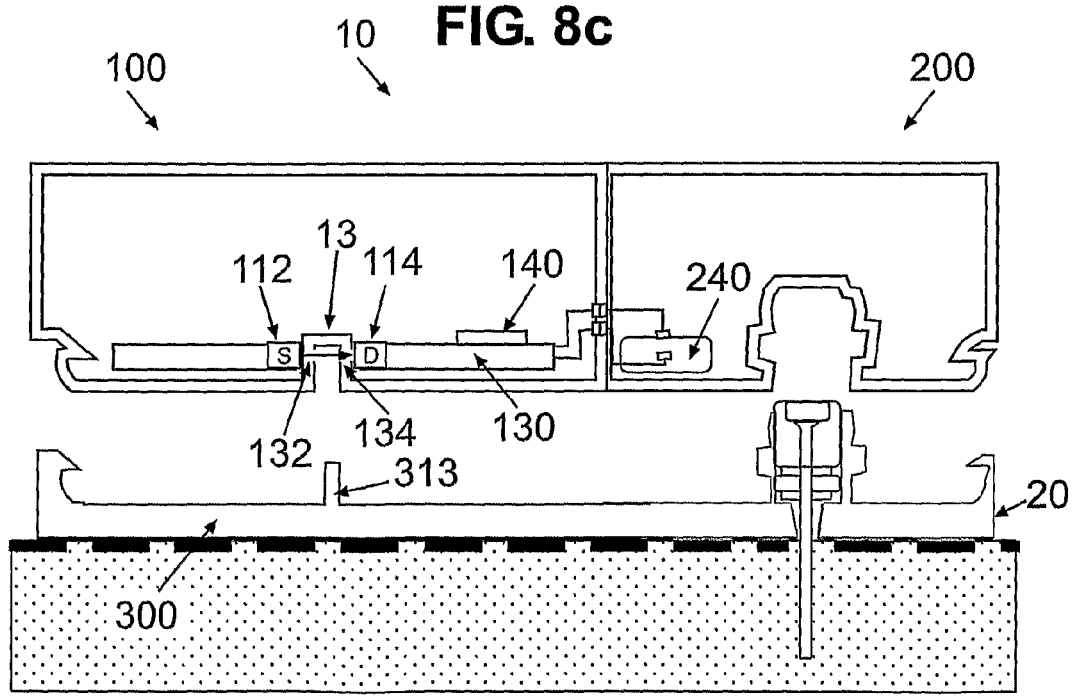
Figure 9B:
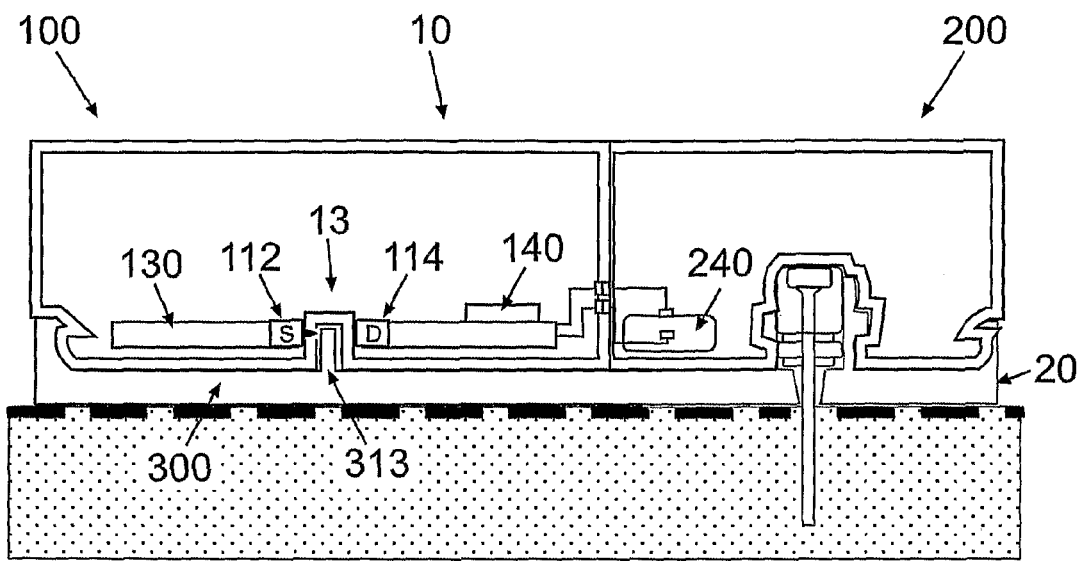

FIGS. 9a-b illustrate another exemplary embodiment of the position detector the operation of which is based on optical sensing, according to the present invention. In this embodiment, the bottom side of the reusable part's (100) housing is configured to have a depression (13). At least two walls (132, 134) of the depression (13) can be fabricated from a transparent material so that light could pass through them. The PCB (130) in this embodiment is configured such that a LED (112) and a light detector (114) can be soldered to the PCB (130) and be situated on opposite sides of the depression (13) thus facing each other. The cradle base (300) is provided with a protrusion (313) configured to fit inside the depression (13) provided in reusable part's (100) housing. FIG. 9a illustrates the patch unit (10) and the cradle unit (20) when they are not connected. In this case, the light emitted by the LED (112) passes through the transparent walls (132, 134) of the depression (13) in the reusable part's (100) housing and is collected by the light detector (114). FIG. 9b shows the patch unit (10) connected to the cradle unit (20). The cradle base's protrusion (313) is located inside the depression (13) in the reusable part's (100) housing, thus preventing light from passing from the LED (112) to the light detector (114). The light emitted by the LED (112) is either absorbed by the protrusion (313) or it is reflected by it, depending on the material it is fabricated from and its color, but in either case no light is collected by the light detector (114). The CPU (not shown) is configured to receive "yes"/"no" light detection signals and accordingly set the patch status to "disconnected" or "connected".

Figure 10A:
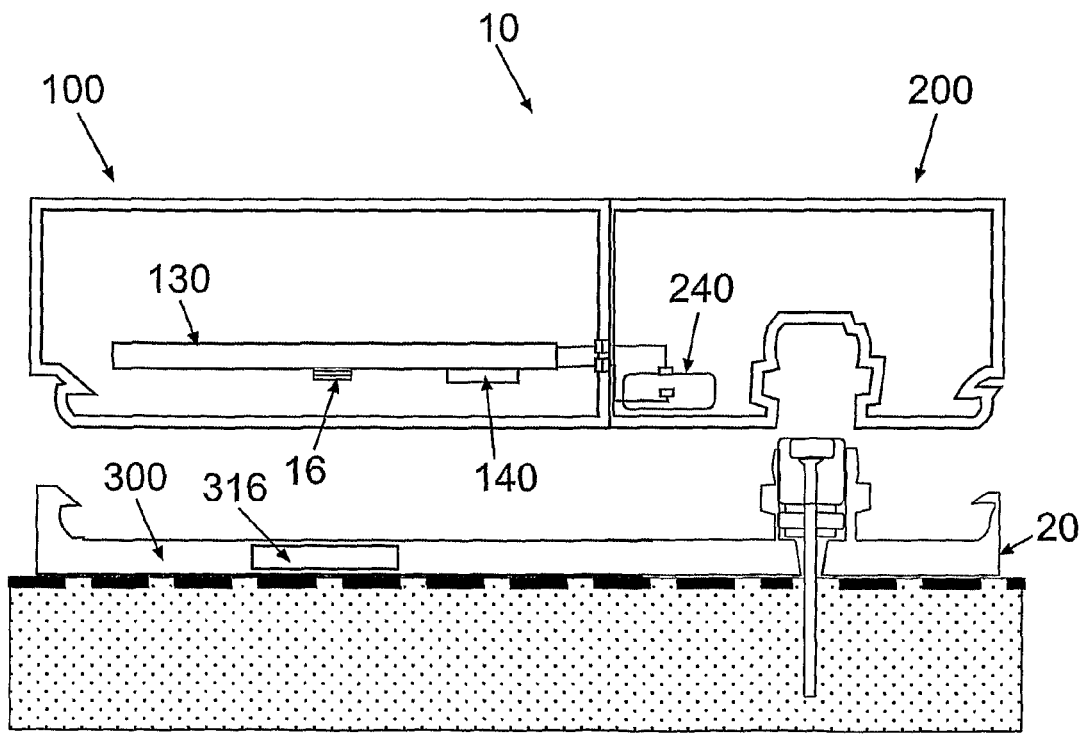
FIGS. 10a-b illustrate an exemplary magnetic position detector.
Figure 10B:
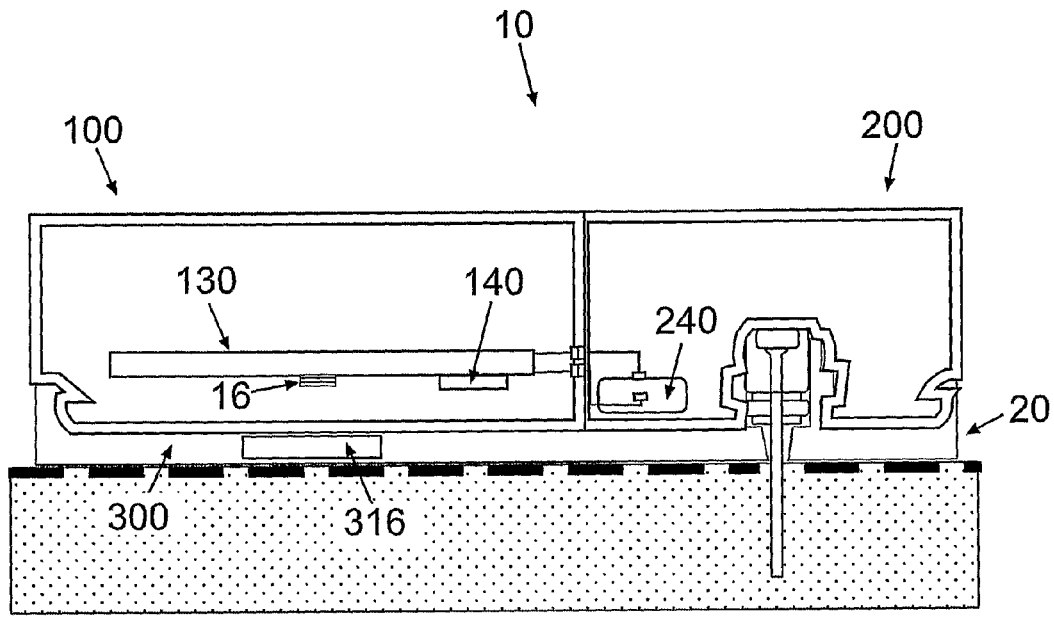

FIGS. 10a-b illustrate another exemplary embodiment of the position detector, according to the present invention. A magnetic field applied by a magnet (316), which is provided in the cradle base (300), affects a magnetic component (16), which is attached to the PCB (130). The magnetic component (16) can be any component that is affected by a magnetic field, for example, an electrical "ON/OFF" Reed switch or a Hall Effect sensor with varying voltage output. The signals generated by the magnetic component are interpreted by the CPU (140) as "connected"/"disconnected" positions and the patch's operation is controlled by the CPU (145) accordingly. FIG. 10a illustrates the patch unit (10) and the cradle unit (20) when they are not connected, and FIG. 10b illustrates the patch unit (10) connected to the cradle unit (20).

Figure 11A:
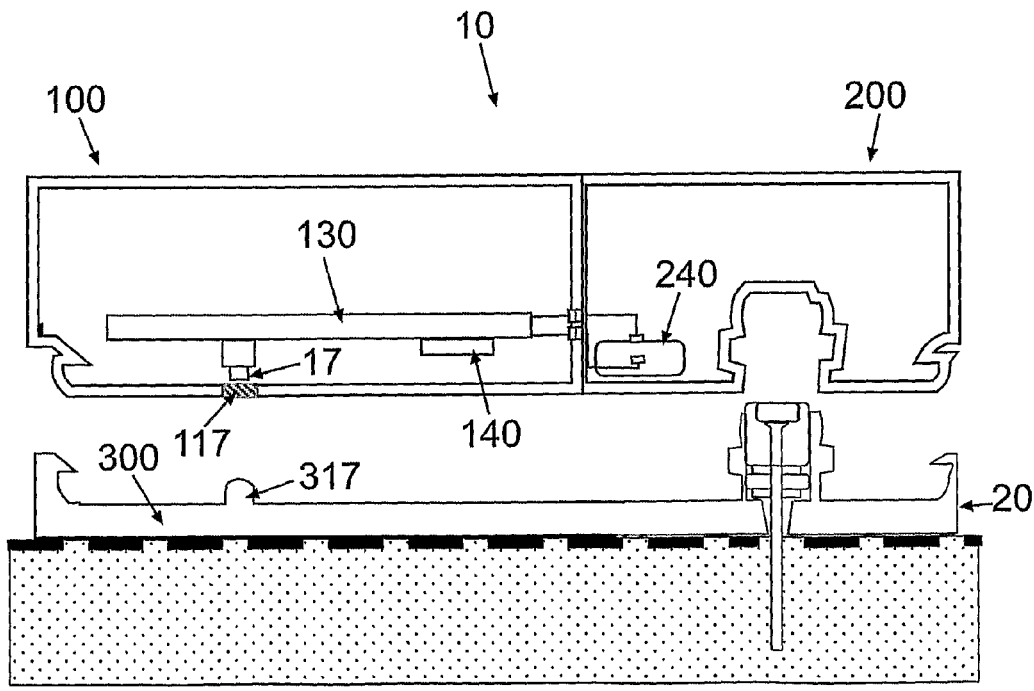
FIGS. 11a-b illustrate an exemplary electro-mechanical position detector.
Figure 11B:
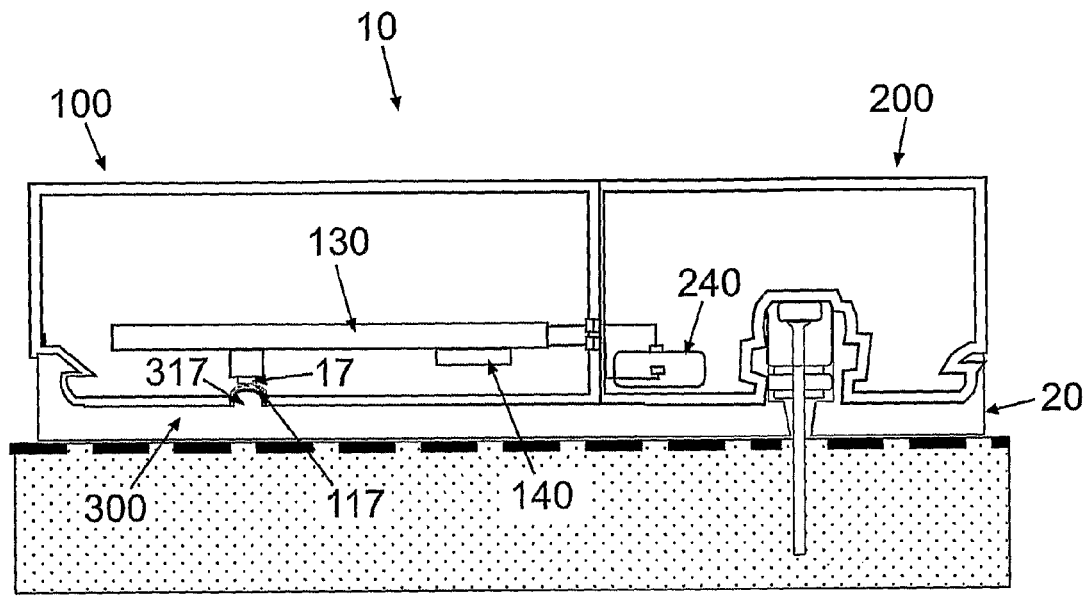

FIGS. 11a-b illustrate an exemplary embodiment of an electro-mechanical position detector, according to the present invention. In this embodiment, an electronic switch (17) is provided, which can be a commercially available tactile switch (e.g., a tact switch manufactured by Alps Electric Co., Ltd., Japan), or any other electronic switch. The switch can be attached to the PCB (130) and connected to the CPU (140). A portion (117) of the reusable part (100) housing, which is located directly beneath the electronic switch (17), may be fabricated from a resilient material, e.g. rubber, preferably using a dedicated molding process so that the patch unit (10) remains water-tight. FIG. 11a and FIG. 11b illustrate the patch (10) and cradle (20) units in "disconnected" and "connected" positions respectively. A protrusion (317) which is provided in the cradle base (300) pushes the resilient portion (117) of the reusable part (100) housing against the electronic switch (17) and turns it in ON or OFF state (depending whether the switch is normally closed or normally open). The state of the electronic switch (17) (ON or OFF) is interpreted by the CPU as "connected"/"disconnected" patch unit position.

Figure 12A:
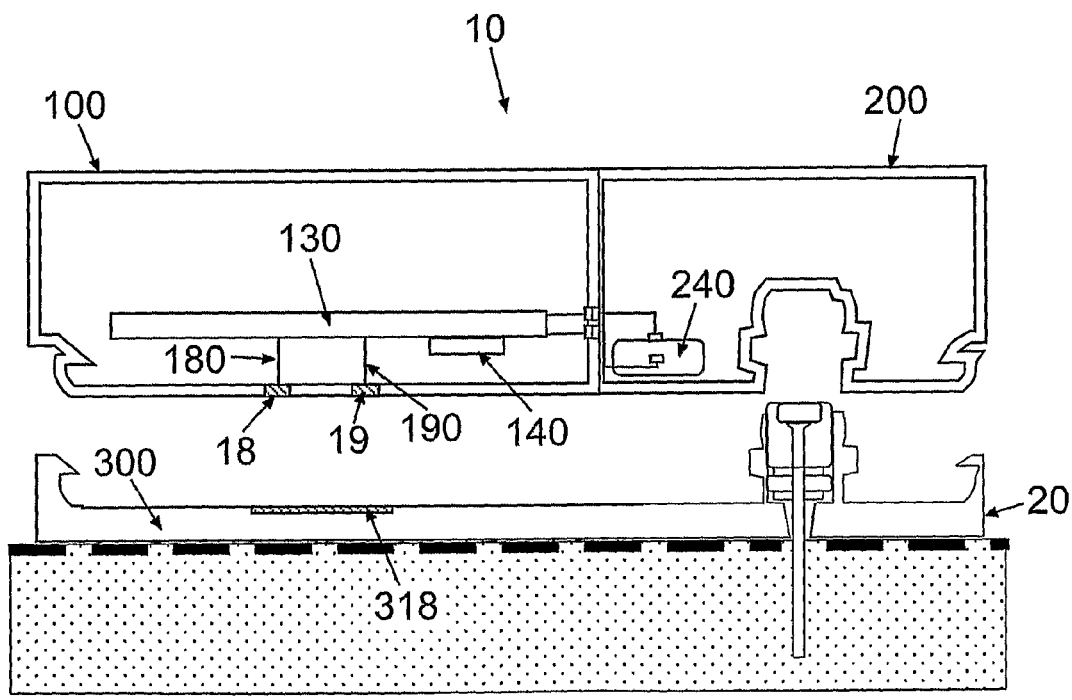
FIGS. 12a-b illustrate an exemplary electronic switch position detector.
Figure 12B:
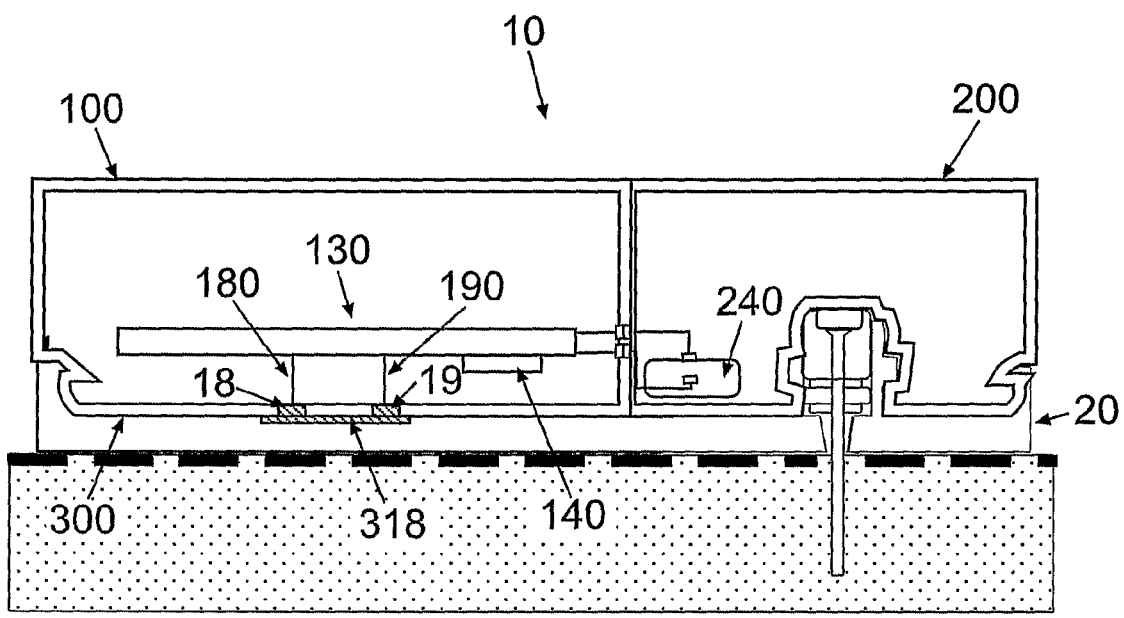

FIGS. 12a-b illustrate another exemplary embodiment of the position detector, which can operate as an electronic switch, according to the present invention. In this embodiment, two electrically conductive surfaces (e.g. fabricated from gold or nickel) (18, 19) can be provided in the reusable part's (100) housing. The conductive surfaces (18, 19) are either embedded in the bottom side of the housing of the reusable part (100), or they are secured thereon by any other suitable method. The conductive surfaces (18, 19) can be configured to be electrically connected to the PCB (130) by appropriate wires (180, 190). A third conductive surface (318) can be either embedded in the cradle base (300) or protruding from the cradle base (300). The area of the third conductive surface (318) can be configured to be large enough to ensure that it contacts both conductive surfaces (18, 19) upon connection of the patch unit (10) and the cradle unit (20). The three conductive surfaces (18, 19 and 318) together constitute an electronic switch. FIG. 12a illustrates the patch unit (10) and the cradle unit (20) when they are not connected. The switch in this case is in an "OFF" state, thus the CPU assigns the patch unit (10) a "disconnected" status. FIG. 12b illustrates the patch unit (10) connected to the cradle unit (20). In this case electrical contact is established between the conductive surfaces (18, 19) and the conductive surface (318), thus the switch is in an "ON" state, and the CPU assigns the patch unit (10) a "connected" status.

It will be noted, that the switch may alternatively be set up such that establishing contact between the reusable part's conductive surfaces (18, 19) and the cradle base's conductive surface (318), would place the switch in an "OFF" state. In such a case, the CPU will assign the patch unit (10) a "connected" status when the switch is in an "OFF" state and a "disconnected" status when the switch is in an "ON" state.

Another embodiment of the present invention may employ a proximity sensor (e.g. an inductive proximity sensor) as a position detector. In case an inductive proximity sensor is employed, the sensor is attached to the PCB, and the cradle base can be provided with a surface fabricated from a magnetic material (e.g., ferromagnetic material), which could be either embedded in the cradle base or protruding from it. The sensor can use a coil or an inductor as a transducer to produce a magnetic field. When the patch unit is in close proximity to the cradle unit, the magnetic surface would be exposed to the sensor's magnetic field. Electrical currents (i.e., Eddy currents) would then build up in the magnetic surface and dampen the sensor's magnetic field. Changes in the magnetic field would result in changes in the sensor's signal output sent to the CPU, and the patch unit's status would be set accordingly. An output threshold can be preprogrammed such that the CPU will set the patch unit's status to "connected" only when the distance between the sensor and the magnetic surface is at its minimum corresponding to a situation when the patch unit is connected to the cradle unit.

Figure 13:
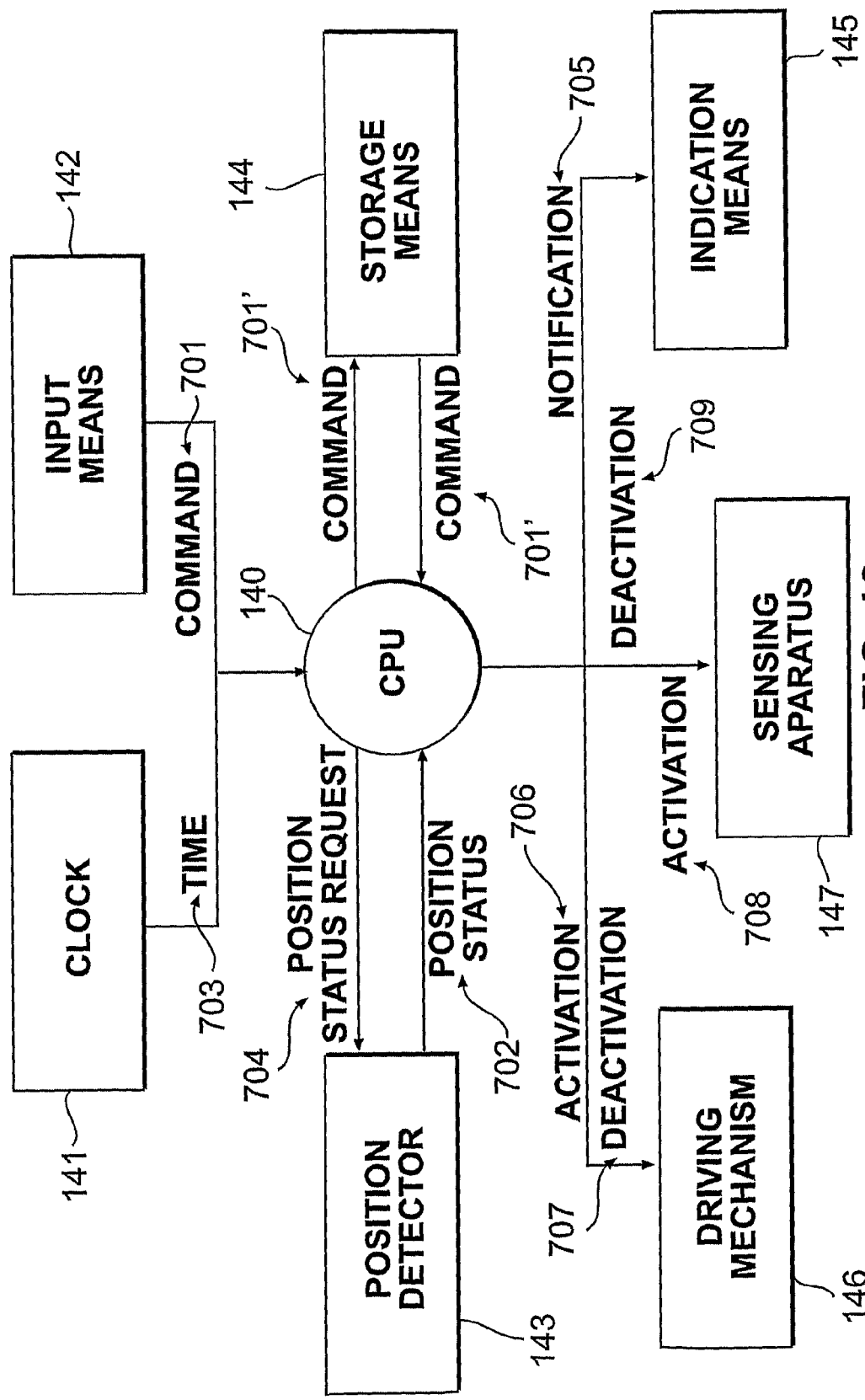
FIG. 13 is a flow chart of exemplary position settings and CPU-controlled patch operations.

FIG. 13 is a flow chart illustrating exemplary method for setting and controlling operation of the patch unit. Position indication (702) is provided by the position detector (143). Position indication (702) can be generated, for example, upon request (704) of the CPU (140), or automatically when the patch unit is being connected/disconnected, or periodically according to a predetermined time schedule. As can be understood by one skilled in the art, other ways of generating position indication signals are possible.

Some steps may be carried out automatically when the patch unit's position is changed. Such steps may include, for example, deactivation or activation (706, 707) of the patch unit's driving mechanism (146) and deactivation or activation of one or more sensing apparatuses (147), as will be demonstrated below. The sensing apparatus (147) can be, for example, a sensor for detecting occlusion in the fluid delivery tube, as described in co-pending, co-owned U.S. patent application Ser. No. 11/810,854 and co-owned International Patent Application No. PCT/IL07/000,684, both filed Jun. 6, 2007, disclosures of which are incorporated herein by reference in their entireties. Other sensing apparatuses may include a sensor for monitoring analyte (e.g., glucose) concentration levels in the patient's body, as disclosed, for example, in co-pending, co-owned U.S. patent application Ser. No. 11/706,606, filed Feb. 14, 2007, disclosure of which is incorporated herein by reference in its entirety.

A notification (as shown in step 705) may be sent to the user via an indication means (145) (e.g. buzzer, visual display) upon position status change and upon activation/deactivation of a patch unit component based on a position status change. The current position (designated by numeral 702' in FIG. 14a) may also be checked after a command (701) has been generated by a user by an input means (142) (e.g. remote control unit or operating buttons provided on the patch unit) and received at the CPU (140). If there is a mismatch between a command (701) and the patch position status (hereinafter "inexecutable command") (e.g. a bolus delivery command is generated when the patch unit and cradle unit are not connected), the command (701) is stored in the storage means (144). The stored command (701') may include additional data, such as command timing (703) provided by a clock (141).

Figure 14A:
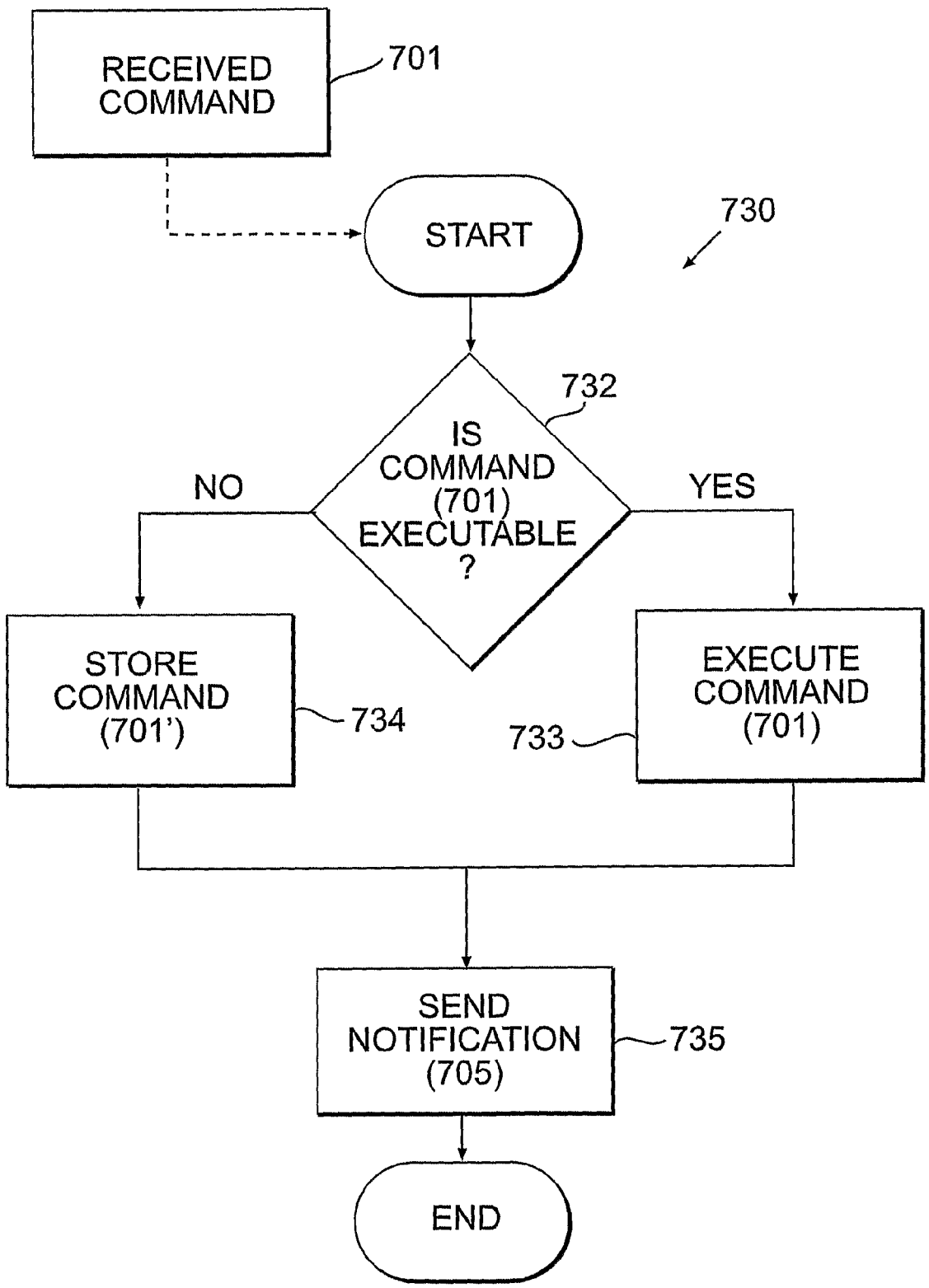
FIGS. 14a-c are flow charts of exemplary processes following position detector indications or inputted commands.

FIG. 14*a* is a flow chart of an exemplary process (730) that takes place after command (701) is received by the CPU. The command (701) is checked (as shown in step 732) in accordance to a current patch position. If the command can be executed, then the execution can be immediately performed (as shown in step 733). If the command cannot be executed, then it can be stored (as shown in step 734) for a later execution. The user can be notified accordingly, as shown in step 735. For example, a bolus delivery command can be received while the patch unit's current status (702') is "disconnected". The command cannot be executed and thus it is stored for a later execution, i.e., upon reconnection of the patch unit to the cradle unit. Appropriate notification can be sent to the patient.

The execution of some commands does not depend on the patch unit's status, i.e., the command can be executed whether the patch is connected or disconnected. An example of such a command is a "set clock" command, which sets the clock of the patch unit according to user input. Some inexecutable commands are not stored for later execution but they are cancelled once they are determined "inexecutable", e.g., a periodical command to sample the occlusion sensor.

Figure 14B:
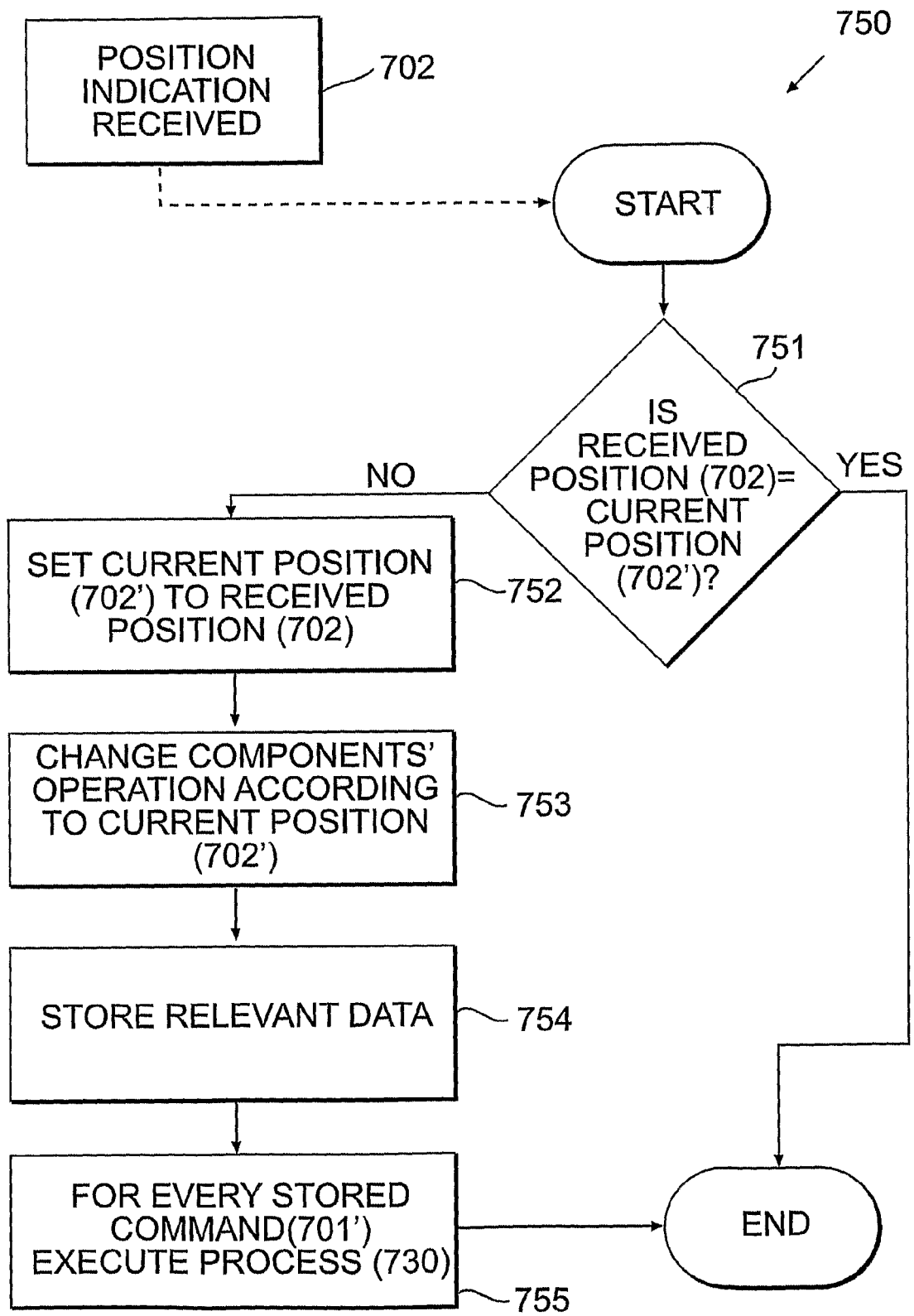

FIG. 14*b* is a flow chart of an exemplary process (750) taking place after receiving position indication (702) from the patch portion of the position indicator (143). If there is a mismatch (as shown in step 751) between the received position (702) and the current position (702'), the following exemplary steps can be carried out in any suitable order:

Step 752: update current position (702');
Step 753: activate or deactivate patch components based on the current position (702');
Step 754: store relevant data (e.g., position change timing);
Step 755: process and execute previously stored commands (701') (e.g., using process 730) according to patch position.

When the patch unit is being disconnected from the cradle unit its position is set to "disconnected" status, the driving mechanism can be deactivated, and timing and amount of undelivered volume can be recorded. If the patch unit is provided with operating buttons and a display, the operating buttons may be unlocked and the display may be activated upon disconnection. After reconnection the patch position can be set to "connected" status, timing is recorded, fluid delivery is resumed, the operating buttons may become locked, and the display may be deactivated.

Figure 14C:
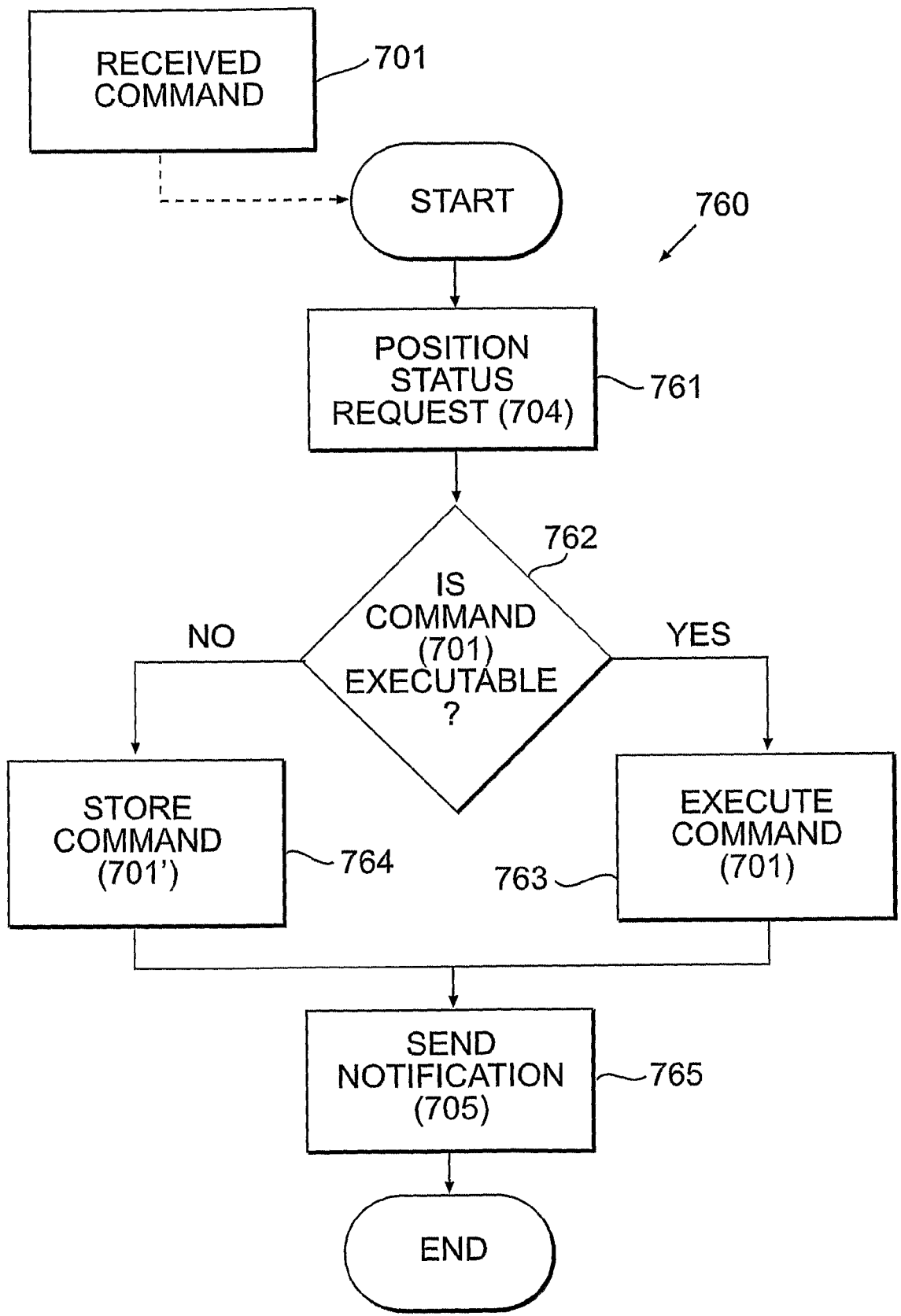

FIG. 14*c* is a flow chart of an exemplary process (760) for position checking after every command (701) is received. The following exemplary steps can be performed by process (760) in any suitable order:

Step 761: send a position status request (704) from the CPU to the position detector, and receive position status indication (702);
Step 762: check command (701) in accordance with received patch position status (702),
Step 763: execute the command if it is executable;
Step 764: store the command if it is inexecutable;
Step 765: notify the patient.

In some embodiments, a bolus delivery command generated by the user can be received at the CPU, and a "disconnected" position status indication (702) can be generated by the position detector. The command cannot be executed, it is therefore stored for later execution, and notification (as shown in step 765) can be sent to the patient. Some inexecutable commands are not stored for a later execution but they are cancelled once they are determined "inexecutable", e.g., a periodical command to sample the occlusion sensor.

As explained above, various position detectors can allow the user to safely disconnect and reconnect the patch unit from and to the cradle unit without using the remote control for suspension or resumption of patch operation, because these actions can be done automatically upon disconnection/reconnection of the patch unit to the cradle unit. The position detector can also prevent the patch unit from operating in case of unintentional disconnection.

A co-owned International Patent Application No. PCT/IL08/001,001, filed Jul. 20, 2008, claiming priority to U.S. Provisional Patent Application No. 60/961,527, filed Jul. 20, 2007, and titled "Manually Operable Portable Infusion Pump" discloses a patch unit having manual button(s) allowing the user to initiate bolus delivery without using the remote control unit. In some embodiments, a dedicated position detector for detecting whether the patch unit is connected to or disconnected from the cradle unit can be used. In other embodiments, a method for controlling the patch unit's operation accordingly can be implemented.

One of the advantages of using some implementations of the detector can be that the user can press the bolus button(s) in a situation when the patch unit is disconnected from the cradle unit and bolus delivery will commence only after the patch unit has been reconnected to the cradle unit.

Figure 15A:
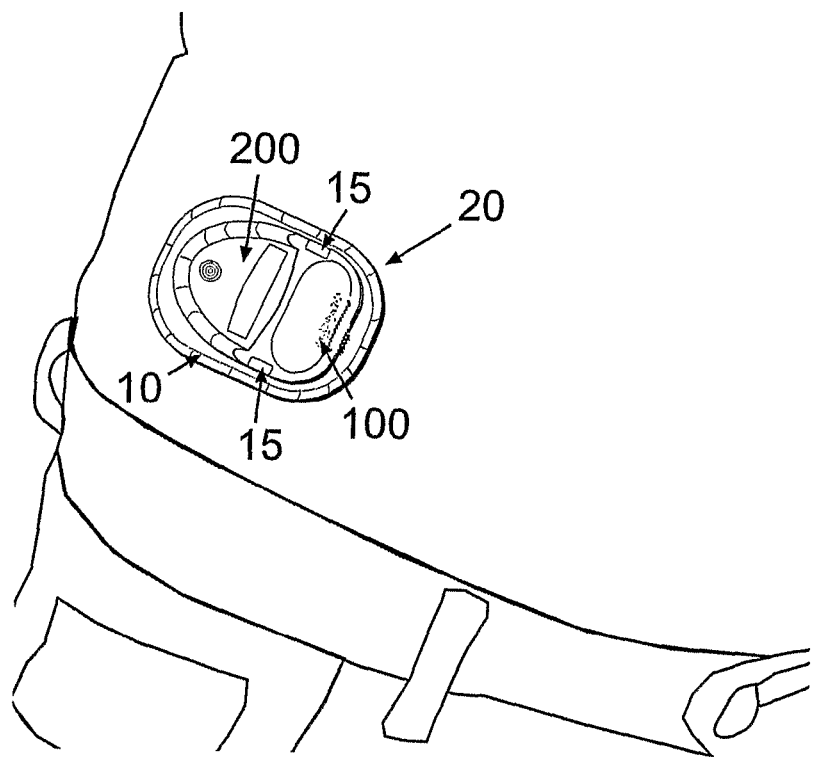
FIGS. 15a-e illustrate an exemplary two-part patch unit provided with manual bolus buttons and a position detector.
Figure 15B:
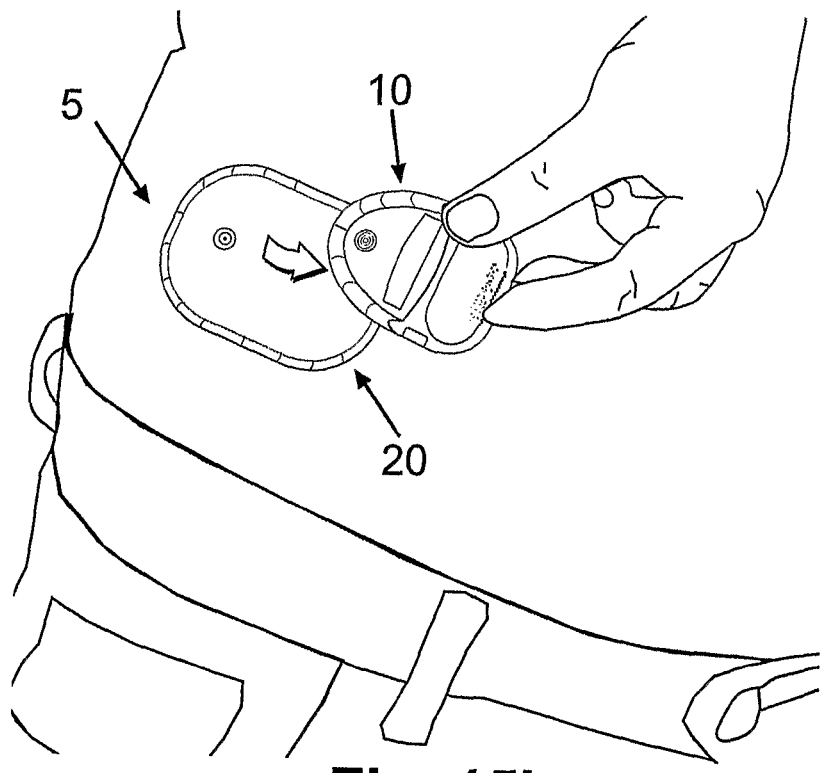
Figure 15C:
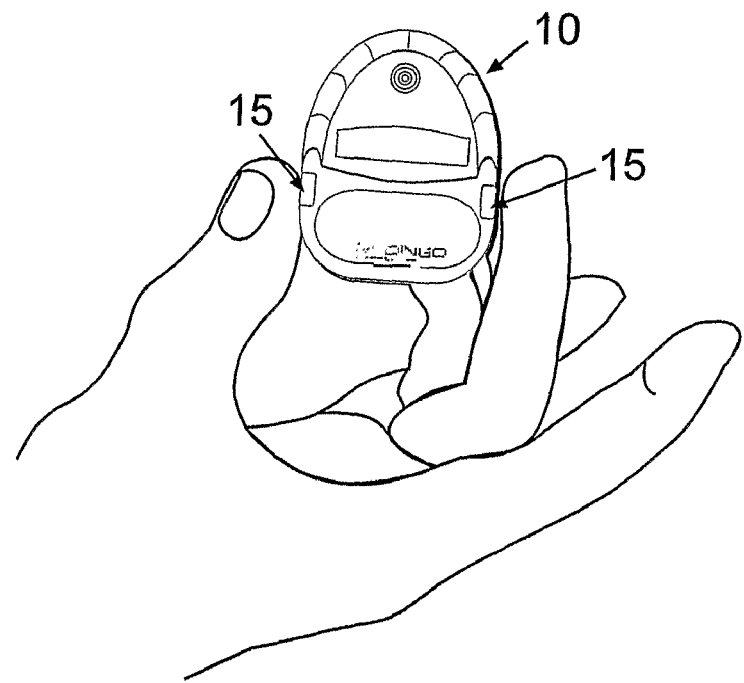
Figure 15D:
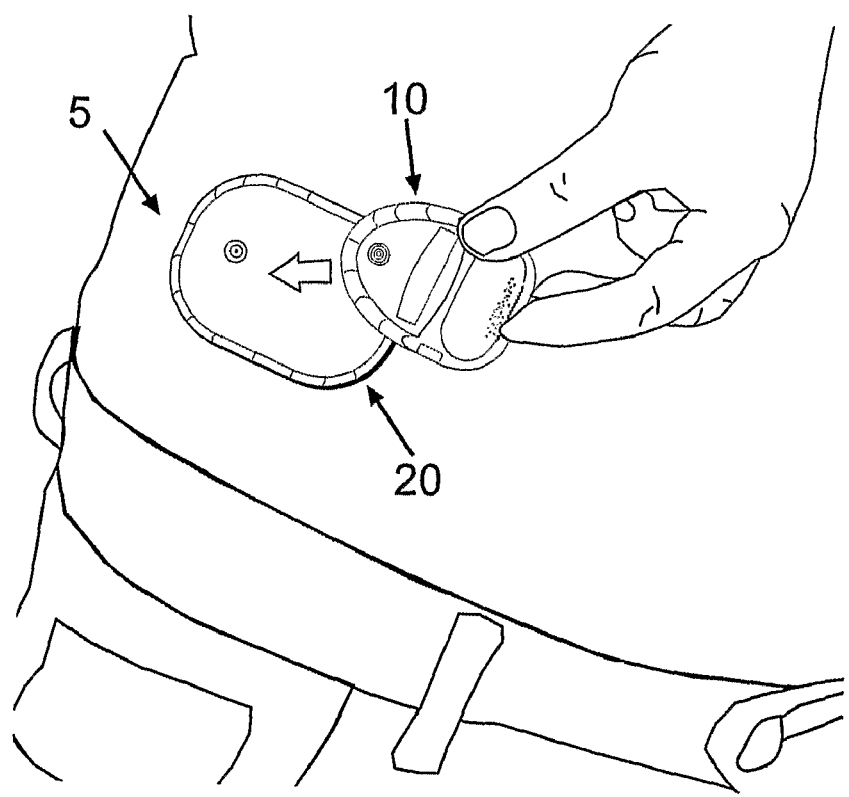
Figure 15E:
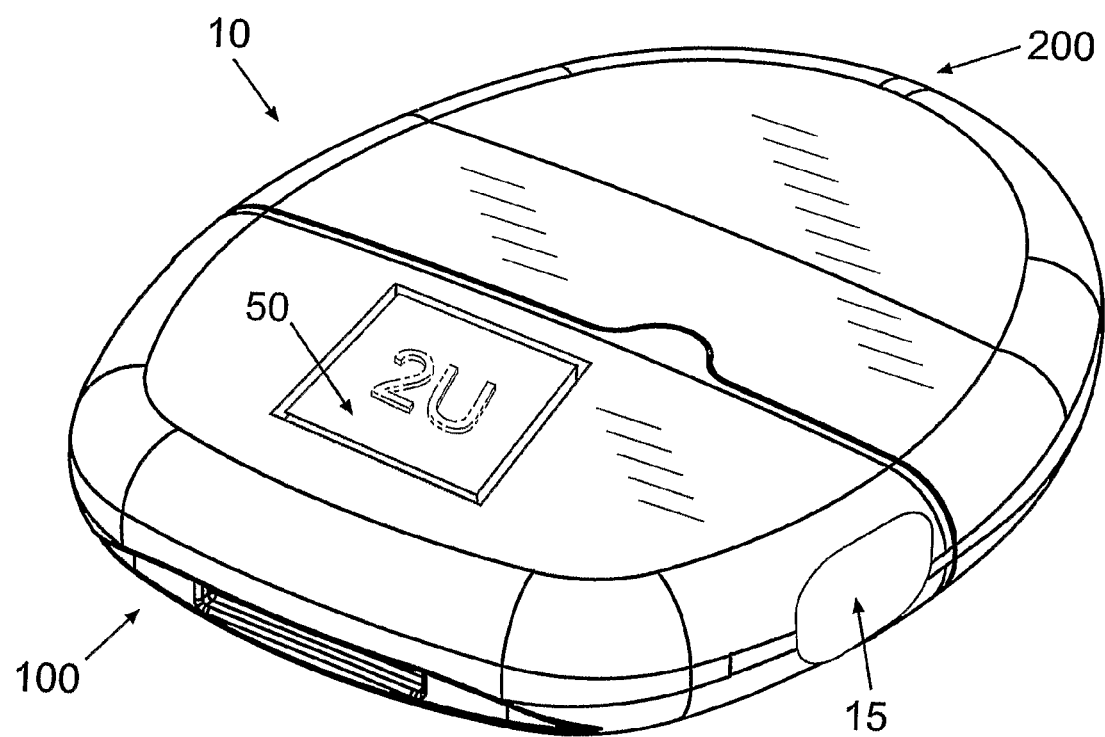
Figure 16A:
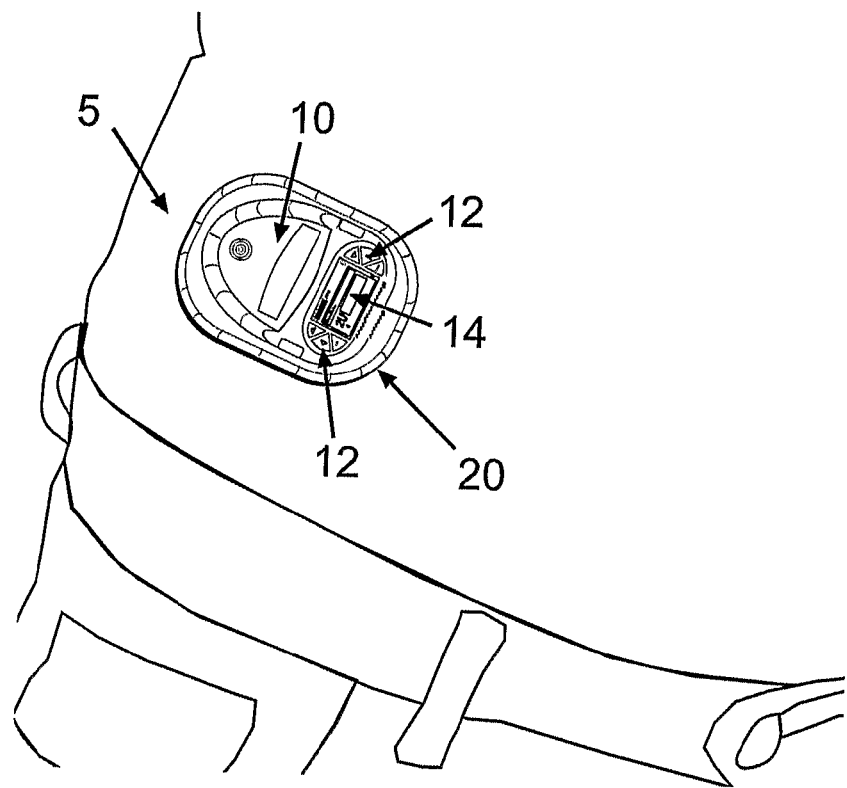
FIGS. 16a-d illustrate an exemplary two-part patch unit provided with operating buttons, a display and a position detector.
Figure 16B:
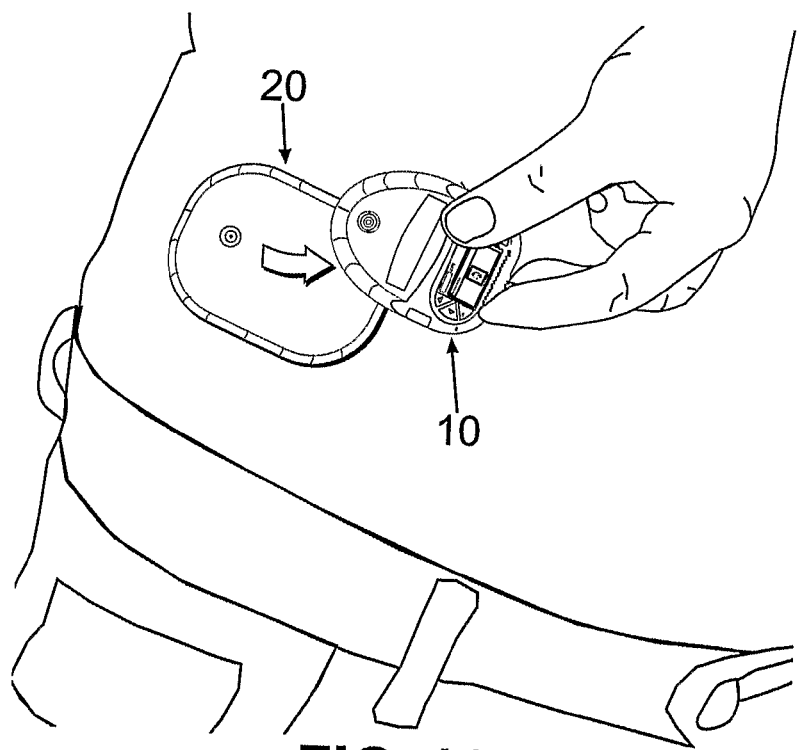
Figure 16C:
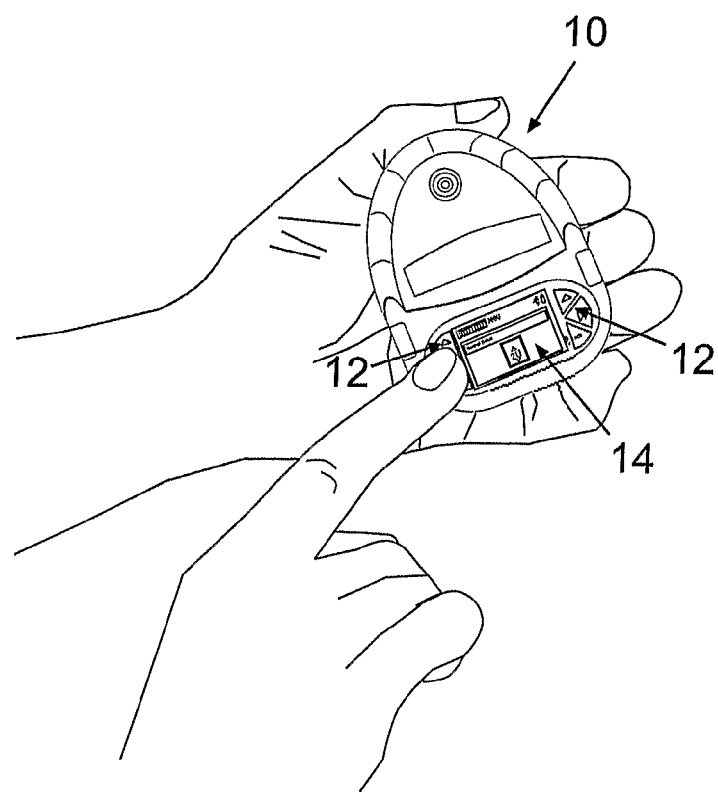
Figure 16D:
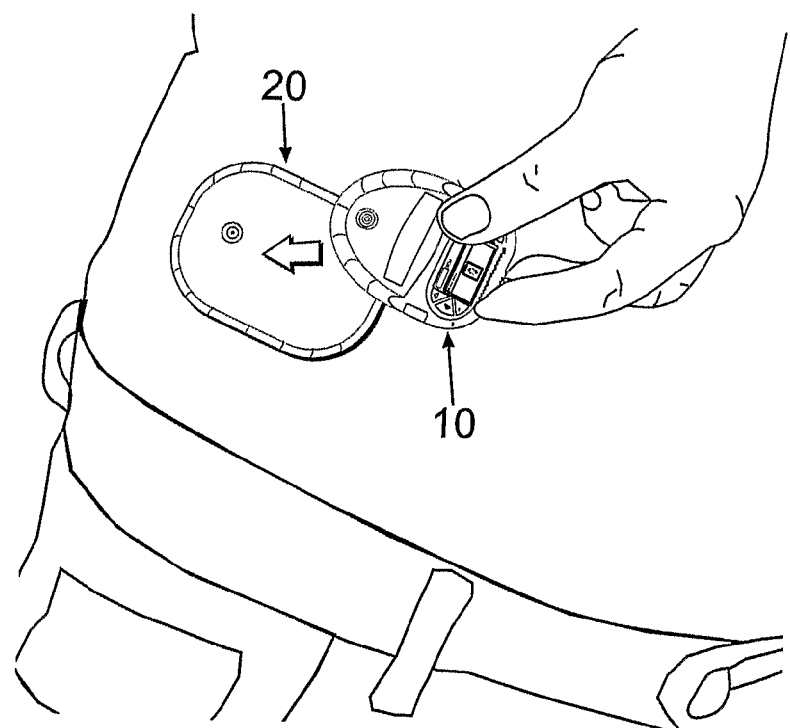

FIGS. 15*a-d* illustrate an exemplary two-part patch unit (10) provided with manual buttons (15) and with a position detector (not shown in the Figures). FIG. 15*a* illustrates an exemplary patch unit (10) connected to a cradle unit (20). FIG. 15*b* illustrates the patch unit (10) being disconnected from the cradle unit (20). FIG. 15*c* illustrates the user simultaneously pressing two bolus buttons (15). FIG. 15*d* illustrates the patch unit (10) being reconnected to the cradle unit (20). FIG. 15*e* illustrates an exemplary embodiment of a two-part patch unit (10) provided with manual bolus buttons (15) and a display (50) on the reusable part's (100) housing. In this exemplary embodiment, the patch unit (10) includes a single part, the display (50) can be positioned anywhere on the patch unit's housing. The display (50) can be configured to show a programmed bolus dosage. In some embodiments, the display (50) can be configured to show additional data, such as the amount of fluid left in the reservoir, the battery status, etc. According to the present invention, if the user presses the bolus buttons (15) when the patch unit (10) is not connected to the cradle unit (20), bolus delivery will not commence until the patch unit (10) is reconnected to the cradle unit (20). The user can therefore attach the cradle unit (20), and consequently the patch unit (10), to the body at remote locations, e.g. the back or buttocks, and still be able to look at the display (50) while pressing the bolus buttons.

A co-owned International Patent Application No. PCT/IL08/001,057, entitled "Portable Infusion Device with Means for Monitoring and Controlling Fluid Delivery", filed Jul. 31, 2008, claiming priority to U.S. Provisional Patent Applications No. 60/963,148, filed on Aug. 1, 2007, and No. 61/004,019, filed on Nov. 21, 2007, both entitled "Portable Infusion Device with Means for Monitoring and Controlling Fluid Delivery", discloses an exemplary embodiment of a patch unit provided with operating buttons and a display which allow the user to control all aspects of both basal and bolus delivery, as well as analyte monitoring in some embodiments, directly from the patch unit without use of a remote control unit.

FIGS. 16a-d illustrate an exemplary two-part patch unit (10) provided with operating buttons (the buttons are designated as a group by numeral 12), a display (14) and a position detector (not seen). In this embodiment the user can disconnect the patch unit (10) from the cradle unit (20), issue the necessary fluid delivery and/or sensing commands using the operating buttons (12) and the display (14), and then reconnect the patch unit (10). In some implementations, the programmed commands can be executed only after the patch unit (10) is reconnected to the cradle unit (20).

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

Any and all of the foregoing patents, applications, and publications referenced in this specification are hereby incorporated by reference herein in their entireties.

What is claimed:

1. A portable therapeutic apparatus securable to the body of a patient comprising:
   a cradle unit attachable to the body of the patient;
   a patch unit configured for removable connection to the cradle unit, the patch unit including at least one housing, a processor and at least one of a fluid delivery pump and an analyte level monitor for sensing a analyte level in the body; and
   a position detector comprising a patch portion and a cradle portion, the patch portion coupled to the patch unit, the cradle portion coupled to or comprising the material of the cradle unit;
   wherein:
      the patch portion of the position detector comprises an electro-mechanical switch and the cradle portion of the position detector comprises an associated switch activation area including a protrusion protruding from a surface of the cradle unit to activate the switch upon connection of the patch unit to the cradle unit,
      the at least on housing of the patch unit includes at least one resilient portion located proximate the switch to enable pressing of the resilient portion against the switch by the protrusion upon connection of the patch unit to the cradle unit,
      the processor is configured for receiving a position indication signal from the position detector, the position indication signal corresponding to a physical proximity of the patch portion to the cradle portion, and
      the portable therapeutic apparatus is configured for at least one therapeutic function selected from the group consisting of delivering a therapeutic fluid into the body of the patient and sensing a bodily analyte.

2. The apparatus according to claim 1, wherein the patch unit further comprises a reusable part and a disposable part connectable to the reusable part, wherein:
   the disposable part comprises a reservoir for storing the therapeutic fluid; and
   the reusable part comprises at least a portion of the fluid delivery pump for delivering the therapeutic fluid from the reservoir into the body of the patient.

3. The apparatus according to claim 2, wherein the patch portion of the position detector is located in the reusable part of the patch unit.

4. The apparatus according to claim 1, wherein the patch unit is configured to be remotely controlled.

5. The apparatus according to claim 1, wherein the patch unit is further provided with at least one manual control switch.

6. The apparatus according to claim 1, wherein the patch unit is further provided with a display.

7. The apparatus according to claim 1, wherein the therapeutic fluid is insulin.

8. The apparatus according to claim 1, wherein the bodily analyte is glucose.

9. The apparatus according to claim 1, wherein the processor is further configured to control at least one component of the apparatus based on the position indication signal received from the position detector.

10. The apparatus according to claim 1, wherein the processor is further configured to control the delivery of the therapeutic fluid into the body of the patient based on the position indication signal received from the position detector.

11. The apparatus according to claim 1, wherein the processor is further configured to deactivate at least one component of the apparatus based on the position indication signal received from the position detector.

12. The apparatus according to claim 1, wherein the processor is further configured to receive at least one command from the patient.

13. The apparatus according to claim 12, wherein the processor is further configured to store the at least one command in a memory.

14. The apparatus according to claim 12, wherein the processor is further configured to notify the patient regarding the at least one command.

15. The apparatus according to claim 1, wherein the processor is further configured to notify the patient regarding the position indication signal.

16. The apparatus according to claim 1, wherein the cradle unit further comprises:
   a cradle base configured as a substantially flat sheet with an adhesive layer facing the skin of the patient and having one or more anchors for connection of the patch unit thereto; and
   a passageway adapted for insertion of a cannula into the body of the patient.

17. The apparatus according to claim 16, wherein the passageway is defined by a well configured to protrude upwardly from the cradle base.

18. The apparatus according to claim 1, wherein the pump comprises a peristaltic pump.

19. The apparatus according to claim 1, wherein the pump comprises a piston pump.

20. The apparatus according to claim 1, wherein the patch portion of the position detector is coupled to a printed circuit board of the patch unit.

21. The apparatus according to claim 1, wherein:
   the cradle unit comprises a plurality of anchoring latches,
   the patch unit comprises a plurality of corresponding recesses configured to receive the plurality of latches upon connection of the patch unit to the cradle unit, and activation of the switch is enabled upon each of the plurality of anchoring latches being received by a recess of the plurality of corresponding recesses.

22. The apparatus according to claim 21, wherein the plurality of anchoring latches comprises two anchoring latched positioned opposite each other.

* * * * *